(12) United States Patent
Yao et al.

(10) Patent No.: US 7,291,485 B2
(45) Date of Patent: Nov. 6, 2007

(54) Gα$_Q$ PROTEIN VARIANTS AND THEIR USE IN THE ANALYSIS AND DISCOVERY OF AGONISTS AND ANTAGONISTS OF CHEMOSENSORY RECEPTORS

(75) Inventors: Yong Yao, San Diego, CA (US); Hong Xu, San Diego, CA (US)

(73) Assignee: Senomyx, Inc., San Diego, CA (US)

( * ) Notice: Subject to any disclaimer, the term of this patent is extended or adjusted under 35 U.S.C. 154(b) by 133 days.

(21) Appl. No.: 10/952,773

(22) Filed: Sep. 30, 2004

(65) Prior Publication Data

US 2005/0136512 A1    Jun. 23, 2005

Related U.S. Application Data

(63) Continuation of application No. 09/984,292, filed on Oct. 29, 2001, now Pat. No. 6,818,747.

(60) Provisional application No. 60/243,770, filed on Oct. 30, 2000.

(51) Int. Cl.
*C12N 15/62* (2006.01)

(52) U.S. Cl. ............... 435/69.7; 435/252.3; 435/320.1; 536/23.4

(58) Field of Classification Search .................. None
See application file for complete search history.

(56) References Cited

OTHER PUBLICATIONS

Mody et al. Incorporation of G alpha z-Specific Sequence at the Carboxyl Terminus Increases the Promiscuity of Galpha16 toward Gi-coupled Receptors. Jan. 2000, Molecular Pharmacology 57:13-23.*
Kostenis et al. Functional Characterization of a Series of Mutant G Protein alpha q Subunits Displaying Promiscuous Receptopr Coupling Properties. J. Biol. Chem. 273(28):17886-17892.*
Strathmann et al. G Protein Diversity: A Distinct Class of alpha Subunits isPresent in Vertibrates and Invertebrates. P.N.A.S. 87:9113-9117.*

* cited by examiner

*Primary Examiner*—John Ulm
(74) *Attorney, Agent, or Firm*—Hunton & Williams LLP

(57) ABSTRACT

The invention provides a series of Gα$_q$ protein variants that functionally couple to sensory cell receptors such as taste GPCRs (TRs) and olfactory GPCRs (ORs) in an overly promiscuous manner. According to the invention, the functional coupling can be determined, for example, by measuring changes in intracellular IP3, or calcium. In a particular embodiment, the Gα$_q$ protein variants can be expressed in mammalian cell lines or *Xenopus* oocytes, and then evaluated using calcium fluorescence imaging and electrophysiological recording.

17 Claims, 8 Drawing Sheets

Fig. 1. Alignment of amino acid sequences of human Gα$_q$, Gα$_{15}$ and Gα$_{16}$ by Clustal method. The matched residues are marked in shaded box. The sequence accession number in the GenBank database is AAB06875, P30678, and P30679 for hGα$_q$, Gα$_{15}$, and Gα$_{16}$ respectively.

```
1    M T L E S I M A C C - - - L S E E A K E A R R I N D E I E R Q L R R D K R D A R    hGq
1    M A R S L T W G C C P W C L T E E E K T A A R I D Q E I N R I L L E Q K K Q E R    G15
1    M A R S L T W R C C P W C L T E D E K A A A R V D Q E I N R I L L E Q K K Q D R    G16

38   R E L K L L L L G T G E S G K S T F I K Q M R I I H G S G Y S D E D K R G F T K    hGq
41   E E L K L L L L G P G E S G K S T F I K Q M R I I H G V G Y S E D R R A F R L      G15
41   G E L K L L L L G P G E S G K S T F I K Q M R I I H G A G Y S E E R K G F R P      G16

78   L V Y Q N I F T A M Q A M I R A M D T L K I P Y K Y E H N K A H A Q L V R E V D    hGq
81   L I Y Q N I F V S M Q A M I D A M D R L Q I P F S R P D S K Q H A S L V M T Q D    G15
81   L V Y Q N I F V S M R A M I E A M E R L Q I P F S R P E S K H H A S L V M S Q D    G16

118  V E K V S A F E N P Y V D A I K S L W N D P G I Q E C Y D R R R E Y Q L S D S T    hGq
121  P Y K V S T F E K P Y A V A M Q Y L W R D A G I R A C Y E R R R E F H L L D S A    G15
121  P Y K V T T F E K R Y A A A M Q W L W R D A G I R A C Y E R R R E F H L L D S A    G16

158  K Y Y L N D L D R V A D P A Y L P T Q Q D V L R V R V P T T G I I E Y P F D L Q    hGq
161  V Y Y L S H L E R I S E D S Y I P T A Q D V L R S R M P T T G I N E Y C F S V K    G15
161  V Y Y L S H L E R I T E E G Y V P T A Q D V L R S R M P T T G I N E Y C F S V Q    G16

198  S V I F R M V D V G G Q R S E R R K W I H C F E N V T S I M F L V A L S E Y D Q    hGq
201  K T K L R I V D V G G Q R S E R R K W I H C F E N V I A L I Y L A S L S E Y D Q    G15
201  K T N L R I V D V G G Q K S E R K K W I H C F E N V I A L I Y L A S L S E Y D Q    G16

238  V L V E S D N E N R M E E S K A L F R T I I T Y P W F Q N S S V I L F L N K K D    hGq
241  C L E E N P Q E N R M E E S L A L F S T I L E L P W F K S T S V I L F L N K T D    G15
241  C L E E N N Q E N R M K E S L A L F G T I L E L P W F K S T S V I L F L N K T D    G16

278  L L E E K I M Y S H L V D Y F P E Y D G P Q R D A Q A A R E F I L K M F V D L -    hGq
281  I L E D K I H T S H L A T Y F P S F Q G P R R D A E A A K S F I L D M Y A R V Y    G15
281  I L E E K I P T S H L A T Y F P S F Q G P K Q D A E A A K R F I L D M Y T R M Y    G16

317  - - - - - N P P S D K I N - - - - - - Y S H F T C A T D T E N I R F V F A A V K    hGq
321  A S C A E P Q D G G R K G S R A R F F A H F T C A T D T Q S V R S V F K D V R      G15
321  T G C V D G P E G S K K G A R S R L F S H Y T C A T D T Q N I R K V F K D V R      G16

346  D T I Q L N L K E Y N L V                                                          hGq
361  P S V L A R Y L D E I N L L                                                        G15
361  P S V L A R Y L D E I N L L                                                        G16
```

Fig. 2. Amino acid sequences of the mouse and human Gα$_q$

1 = mouse
2 = human

1 MTLESIMACCLSEEAKEARRINDEIERQLRRDKRDARRELKLLLLGTGESGKSTFIKQMRIIHGSGYSDE
2 MTLESIMACCLSEEAKEARRINDEIERQLRRDKRDARRELKLLLLGTGESGKSTFIKQMRIIHGSGYSDE

DKRGFTKLVYQNIFTAMQAMIRAMDTLKIPYKYEHNKAHAQLVREVDVEKVSAFENPYVDAIKSLWNDPG
DKRGFTKLVYQNIFTAMQAMIRAMDTLKIPYKYEHNKAHAQLVREVDVEKVSAFENPYVDAIKSLWNDPG

IQECYDRRREYQLSDSTKYYLNDLDRVADPSYLPTQQDVLRVRVPTTGIIEYPFDLQSVIFRMVDVGGQR
IQECYDRRREYQLSDSTKYYLNDLDRVADPAYLPTQQDVLRVRVPTTGIIEYPFDLQSVIFRMVDVGGQR

SERRKWIHCFENVTSIMFLVALSEYDQVLVESDNENRMEESKALFRTIITYPWFQNSSVILFLNKKDLLE
SERRKWIHCFENVTSIMFLVALSEYDQVLVESDNENRMEESKALFRTIITYPWFQNSSVILFLNKKDLLE

EKIMYSHLVDYFPEYDGPQRDAQAAREFILKMFVDLNPDSDKIIYSHFTCATDTENIRFVFAAVKDTILQ
EKIMYSHLVDYFPEYDGPQRDAQAAREFILKMFVDLNPDSDKIIYSHFTCATDTENIRFVFAAVKDTILQ

LNLKEYNLV
LNLKEYNLV

Key amino acids described in this invention are boxed
Difference between human and mouse is underlined

FIGURE 3A

Amino acid sequences of the mouse and human Gα$_q$ proteins tested. Variation of amino acids of Gα$_q$ is depicted in parenthesis. The sequence numbers of amino acid H or Q, V or L are 28 and 29 respectively. The sequence number of amino acid G or D is 66. Truncation of N-terminal six amino acids (MTLESI) are shown as ΔN. Hemaglutinin (HA) epitope tag (DVPDYA) spans from 125 to 130. C-terminal five amino acids (-t5) or 44 amino acids (-t44) of transducin and five amino acids of Gα$_{olf}$ (-olf5) are used respectively to replace those of Gα$_q$.

Mouse sequences created and tested:

Sequence ID#1
mGq
MTLESIMACCLSEEAKEARRINDEIERQLRRDKRDARRELKLLLLGTGESGKSTFIKQMRIIHGSGYSDE
DKRGFTKLVYQNIFTAMQAMIRAMDTLKIPYKYEHNKAHAQLVREVDVEKVSAFENPYVDAIKSLWNDPG
IQECYDRRREYQLSDSTKYYLNDLDRVADPSYLPTQQDVLRVRVPTTGIIEYPFDLQSVIFRMVDVGGQR
SERRKWIHCFENVTSIMFLVALSEYDQVLVESDNENRMEESKALFRTIITYPWFQNSSVILFLNKKDLLE
EKIMYSHLVDYFPEYDGPQRDAQAAREFILKMFVDLNPDSDKIIYSHFTCATDTENIRFVFAAVKDTILQ
LNLKEYNLV Sequence ID#2
mGq (ΔN)
        MACCLSEEAKEARRINDEIERQLRRDKRDARRELKLLLLGTGESGKSTFIKQMRIIHGSGYSDE
DKRGFTKLVYQNIFTAMQAMIRAMDTLKIPYKYEHNKAHAQLVREVDVEKVSAFENPYVDAIKSLWNDPG
IQECYDRRREYQLSDSTKYYLNDLDRVADPSYLPTQQDVLRVRVPTTGIIEYPFDLQSVIFRMVDVGGQR
SERRKWIHCFENVTSIMFLVALSEYDQVLVESDNENRMEESKALFRTIITYPWFQNSSVILFLNKKDLLE
EKIMYSHLVDYFPEYDGPQRDAQAAREFILKMFVDLNPDSDKIIYSHFTCATDTENIRFVFAAVKDTILQ
LNLKEYNLV Sequence ID#3
mGq (HA)
MTLESIMACCLSEEAKEARRINDEIERQLRRDKRDARRELKLLLLGTGESGKSTFIKQMRIIHGSGYSDE
DKRGFTKLVYQNIFTAMQAMIRAMDTLKIPYKYEHNKAHAQLVREVDVEKVSAFDVPDYAAIKSLWNDPG
IQECYDRRREYQLSDSTKYYLNDLDRVADPSYLPTQQDVLRVRVPTTGIIEYPFDLQSVIFRMVDVGGQR
SERRKWIHCFENVTSIMFLVALSEYDQVLVESDNENRMEESKALFRTIITYPWFQNSSVILFLNKKDLLE
EKIMYSHLVDYFPEYDGPQRDAQAAREFILKMFVDLNPDSDKIIYSHFTCATDTENIRFVFAAVKDTILQ
LNLKEYNLV Sequence ID#4
mGq (ΔN-HA)
        MACCLSEEAKEARRINDEIERQLRRDKRDARRELKLLLLGTGESGKSTFIKQMRIIHGSGYSDE
DKRGFTKLVYQNIFTAMQAMIRAMDTLKIPYKYEHNKAHAQLVREVDVEKVSAFDVPDYAAIKSLWNDPG
IQECYDRRREYQLSDSTKYYLNDLDRVADPSYLPTQQDVLRVRVPTTGIIEYPFDLQSVIFRMVDVGGQR
SERRKWIHCFENVTSIMFLVALSEYDQVLVESDNENRMEESKALFRTIITYPWFQNSSVILFLNKKDLLE
EKIMYSHLVDYFPEYDGPQRDAQAAREFILKMFVDLNPDSDKIIYSHFTCATDTENIRFVFAAVKDTILQ
LNLKEYNLV Sequence ID#5
mGq(ΔN-HVD-HA) from Kostenis et al 1998
        MACCLSEEAKEARRINDEIERHVRRDKRDARRELKLLLLGTGESGKSTFIKQMRIIHGSDYSDE
DKRGFTKLVYQNIFTAMQAMIRAMDTLKIPYKYEHNKAHAQLVREVDVEKVSAFDVPDYAAIKSLWNDPG

FIGURE 3B

```
IQECYDRRREYQLSDSTKYYLNDLDRVADPSYLPTQQDVLRVRVPTTGIIEYPFDLQSVIFRMVDVGGQR
SERRKWIHCFENVTSIMFLVALSEYDQVLVESDNENRMEESKALFRTIITYPWFQNSSVILFLNKKDLLE
EKIMYSHLVDYFPEYDGPQRDAQAAREFILKMFVDLNPDSDKIIYSHFTCATDTENIRFVFAAVKDTILQ
LNLKEYNLV
```

Sequence ID#6 mGq(ΔN-HVD-HA)-t5

```
    MACCLSEEAKEARRINDEIERHVRRDKRDARRELKLLLLGTGESGKSTFIKQMRIIHGSDYSDE
DKRGFTKLVYQNIFTAMQAMIRAMDTLKIPYKYEHNKAHAQLVREVDVEKVSAFDVPDYAAIKSLWNDPG
IQECYDRRREYQLSDSTKYYLNDLDRVADPSYLPTQQDVLRVRVPTTGIIEYPFDLQSVIFRMVDVGGQR
SERRKWIHCFENVTSIMFLVALSEYDQVLVESDNENRMEESKALFRTIITYPWFQNSSVILFLNKKDLLE
EKIMYSHLVDYFPEYDGPQRDAQAAREFILKMFVDLNPDSDKIIYSHFTCATDTENIRFVFAAVKDTILQ
LNLKDCGLF
```

Sequence ID#7 mGq(ΔN-HVD-HA)-t44

```
    MACCLSEEAKEARRINDEIERHVRRDKRDARRELKLLLLGTGESGKSTFIKQMRIIHGSDYSDE
DKRGFTKLVYQNIFTAMQAMIRAMDTLKIPYKYEHNKAHAQLVREVDVEKVSAFDVPDYAAIKSLWNDPG
IQECYDRRREYQLSDSTKYYLNDLDRVADPSYLPTQQDVLRVRVPTTGIIEYPFDLQSVIFRMVDVGGQR
SERRKWIHCFENVTSIMFLVALSEYDQVLVESDNENRMEESKALFRTIITYPWFQNSSVILFLNKKDLLE
EKIMYSHLVDYFPEYDGPQRDAQAAREFILKMFVDNMRRDVKEIYSHMTCATDTQNVKFVFDAVTDIIIK
ENLKDCGLF
```

Sequence ID#8 mGq(ΔN-HVG-HA)

```
    MACCLSEEAKEARRINDEIERHVRRDKRDARRELKLLLLGTGESGKSTFIKQMRIIHGSGYSDE
DKRGFTKLVYQNIFTAMQAMIRAMDTLKIPYKYEHNKAHAQLVREVDVEKVSAFDVPDYAAIKSLWNDPG
IQECYDRRREYQLSDSTKYYLNDLDRVADPSYLPTQQDVLRVRVPTTGIIEYPFDLQSVIFRMVDVGGQR
SERRKWIHCFENVTSIMFLVALSEYDQVLVESDNENRMEESKALFRTIITYPWFQNSSVILFLNKKDLLE
EKIMYSHLVDYFPEYDGPQRDAQAAREFILKMFVDLNPDSDKIIYSHFTCATDTENIRFVFAAVKDTILQ
LNLKEYNLV
```

Sequence ID#9 mGq(HVG-HA)

```
MTLESIMACCLSEEAKEARRINDEIERHVRRDKRDARRELKLLLLGTGESGKSTFIKQMRIIHGSGYSDE
DKRGFTKLVYQNIFTAMQAMIRAMDTLKIPYKYEHNKAHAQLVREVDVEKVSAFDVPDYAAIKSLWNDPG
IQECYDRRREYQLSDSTKYYLNDLDRVADPSYLPTQQDVLRVRVPTTGIIEYPFDLQSVIFRMVDVGGQR
SERRKWIHCFENVTSIMFLVALSEYDQVLVESDNENRMEESKALFRTIITYPWFQNSSVILFLNKKDLLE
EKIMYSHLVDYFPEYDGPQRDAQAAREFILKMFVDLNPDSDKIIYSHFTCATDTENIRFVFAAVKDTILQ
LNLKEYNLV
```

Sequence ID#10 mGq(D-HA)

```
MTLESIMACCLSEEAKEARRINDEIERQLRRDKRDARRELKLLLLGTGESGKSTFIKQMRIIHGSDYSDE
DKRGFTKLVYQNIFTAMQAMIRAMDTLKIPYKYEHNKAHAQLVREVDVEKVSAFDVPDYAAIKSLWNDPG
IQECYDRRREYQLSDSTKYYLNDLDRVADPSYLPTQQDVLRVRVPTTGIIEYPFDLQSVIFRMVDVGGQR
SERRKWIHCFENVTSIMFLVALSEYDQVLVESDNENRMEESKALFRTIITYPWFQNSSVILFLNKKDLLE
EKIMYSHLVDYFPEYDGPQRDAQAAREFILKMFVDLNPDSDKIIYSHFTCATDTENIRFVFAAVKDTILQ
LNLKEYNLV
```

Sequence ID#11

FIGURE 3C

.mGq'(HVD-HA)
MTLESIMACCLSEEAKEARRINDEIERHVRRDKRDARRELKLLLLGTGESGKSTFIKQMRIIHGSDYSDE
DKRGFTKLVYQNIFTAMQAMIRAMDTLKIPYKYEHNKAHAQLVREVDVEKVSAFDVPDYAAIKSLWNDPG
IQECYDRRREYQLSDSTKYYLNDLDRVADPSYLPTQQDVLRVRVPTTGIIEYPFDLQSVIFRMVDVGGQR
SERRKWIHCFENVTSIMFLVALSEYDQVLVESDNENRMEESKALFRTIITYPWFQNSSVILFLNKKDLLE
EKIMYSHLVDYFPEYDGPQRDAQAAREFILKMFVDLNPDSDKIIYSHFTCATDTENIRFVFAAVKDTILQ
LNLKEYNLV

Sequence ID#12
mGq(HVG-HA)-t5
MTLESIMACCLSEEAKEARRINDEIERHVRRDKRDARRELKLLLLGTGESGKSTFIKQMRIIHGSGYSDE
DKRGFTKLVYQNIFTAMQAMIRAMDTLKIPYKYEHNKAHAQLVREVDVEKVSAFDVPDYAAIKSLWNDPG
IQECYDRRREYQLSDSTKYYLNDLDRVADPSYLPTQQDVLRVRVPTTGIIEYPFDLQSVIFRMVDVGGQR
SERRKWIHCFENVTSIMFLVALSEYDQVLVESDNENRMEESKALFRTIITYPWFQNSSVILFLNKKDLLE
EKIMYSHLVDYFPEYDGPQRDAQAAREFILKMFVDLNPDSDKIIYSHFTCATDTENIRFVFAAVKDTILQ
LNLKDCGLF Sequence ID#13
mGq(HVD-HA)-t5
MTLESIMACCLSEEAKEARRINDEIERHVRRDKRDARRELKLLLLGTGESGKSTFIKQMRIIHGSDYSDE
DKRGFTKLVYQNIFTAMQAMIRAMDTLKIPYKYEHNKAHAQLVREVDVEKVSAFDVPDYAAIKSLWNDPG
IQECYDRRREYQLSDSTKYYLNDLDRVADPSYLPTQQDVLRVRVPTTGIIEYPFDLQSVIFRMVDVGGQR
SERRKWIHCFENVTSIMFLVALSEYDQVLVESDNENRMEESKALFRTIITYPWFQNSSVILFLNKKDLLE
EKIMYSHLVDYFPEYDGPQRDAQAAREFILKMFVDLNPDSDKIIYSHFTCATDTENIRFVFAAVKDTILQ
LNLKDCGLF Sequence ID#14
mGq(ΔN-HVD-HA)-olf5
        MACCLSEEAKEARRINDEIERHVRRDKRDARRELKLLLLGTGESGKSTFIKQMRIIHGSDYSDE
DKRGFTKLVYQNIFTAMQAMIRAMDTLKIPYKYEHNKAHAQLVREVDVEKVSAFDVPDYAAIKSLWNDPG
IQECYDRRREYQLSDSTKYYLNDLDRVADPSYLPTQQDVLRVRVPTTGIIEYPFDLQSVIFRMVDVGGQR
SERRKWIHCFENVTSIMFLVALSEYDQVLVESDNENRMEESKALFRTIITYPWFQNSSVILFLNKKDLLE
EKIMYSHLVDYFPEYDGPQRDAQAAREFILKMFVDLNPDSDKIIYSHFTCATDTENIRFVFAAVKDTILQ
LNLKQYELL Human Sequences Tested Sequence ID#15
hGq
MTLESIMACCLSEEAKEARRINDEIERQLRRDKRDARRELKLLLLGTGESGKSTFIKQMRIIHGSGYSDE
DKRGFTKLVYQNIFTAMQAMIRAMDTLKIPYKYEHNKAHAQLVREVDVEKVSAFENPYVDAIKSLWNDPG
IQECYDRRREYQLSDSTKYYLNDLDRVADPAYLPTQQDVLRVRVPTTGIIEYPFDLQSVIFRMVDVGGQR
SERRKWIHCFENVTSIMFLVALSEYDQVLVESDNENRMEESKALFRTIITYPWFQNSSVILFLNKKDLLE
EKIMYSHLVDYFPEYDGPQRDAQAAREFILKMFVDLNPDSDKIIYSHFTCATDTENIRFVFAAVKDTILQ
LNLKEYNAV Sequence ID#16
hGq(ΔN)
        MACCLSEEAKEARRINDEIERQLRRDKRDARRELKLLLLGTGESGKSTFIKQMRIIHGSGYSDE
DKRGFTKLVYQNIFTAMQAMIRAMDTLKIPYKYEHNKAHAQLVREVDVEKVSAFENPYVDAIKSLWNDPG
IQECYDRRREYQLSDSTKYYLNDLDRVADPAYLPTQQDVLRVRVPTTGIIEYPFDLQSVIFRMVDVGGQR

FIGURE 3D

SERRKWIHCFENVTSIMFLVALSEYDQVLVESDNENRMEESKALFRTIITYPWFQNSSVILFLNKKDLLE
EKIMYSHLVDYFPEYDGPQRDAQAAREFILKMFVDLNPDSDKIIYSHFTCATDTENIRFVFAAVKDTILQ
LNLKEYNAV

Table I: Function Activity Of Gαq Variants Tested

| Gq Variants | Seq ID # | Functional Activity with Taste Receptor mT2R5 | Functional Activity with Olfactory Receptor mI7 |
|---|---|---|---|
| mGq | 1 | - | Not tested |
| mGq(ΔN) | 2 | - | Not tested |
| mGq(HA) | 3 | - | Not tested |
| mGq(ΔN-HA) | 4 | - | Not tested |
| mGq(ΔN-HVD-HA) | 5 | + | + |
| mGq(ΔN-HVD-HA)-t5 | 6 | ++ | Not tested |
| mGq(ΔN-HVD-HA)-t44 | 7 | ++ | Not tested |
| mGq(ΔN-HV-HA) | 8 | - | Not tested |
| mGq(HV-HA) | 9 | - | Not tested |
| mGq(D-HA) | 10 | + | Not tested |
| mGq(HVD-HA) | 11 | + | Not tested |
| mGq(HV-HA)-t5 | 12 | + | Not tested |
| mGq(HVD-HA)-t5 | 13 | ++ | Not tested |
| mGq(ΔN-HVD-HA)-olf5 | 14 | Not tested | ++ |
| hGq | 15 | - | Not tested |
| hGq(ΔN) | 16 | - | Not tested |

+ means functionally couples with chemosensory receptor
++ means functionally couples with chemosensory receptor
- means does not functionally couple

FIGURE 4A

Other sequences predicted by this invention active in assays of chemosensory receptors such as those GPCRs involved in sensing of tastants, olfactants and pheromones.

Sequence ID#17
hGq(ΔN-HVD-HA)
 MACCLSEEAKEARRINDEIERHVRRDKRDARRELKLLLLGTGESGKSTFIKQMRIIHGSDYSDE
DKRGFTKLVYQNIFTAMQAMIRAMDTLKIPYKYEHNKAHAQLVREVDVEKVSAFDVPDYAAIKSLWNDPG
IQECYDRRREYQLSDSTKYYLNDLDRVADPAYLPTQQDVLRVRVPTTGIIEYPFDLQSVIFRMVDVGGQR
SERRKWIHCFENVTSIMFLVALSEYDQVLVESDNENRMEESKALFRTIITYPWFQNSSVILFLNKKDLLE
EKIMYSHLVDYFPEYDGPQRDAQAAREFILKMFVDLNPDSDKIIYSHFTCATDTENIRFVFAAVKDTILQ
LNLKEYNLV Sequence ID#18
hGq(ΔN-HVD-HA)-t5
 MACCLSEEAKEARRINDEIERHVRRDKRDARRELKLLLLGTGESGKSTFIKQMRIIHGSDYSDE
DKRGFTKLVYQNIFTAMQAMIRAMDTLKIPYKYEHNKAHAQLVREVDVEKVSAFDVPDYAAIKSLWNDPG
IQECYDRRREYQLSDSTKYYLNDLDRVADPAYLPTQQDVLRVRVPTTGIIEYPFDLQSVIFRMVDVGGQR
SERRKWIHCFENVTSIMFLVALSEYDQVLVESDNENRMEESKALFRTIITYPWFQNSSVILFLNKKDLLE
EKIMYSHLVDYFPEYDGPQRDAQAAREFILKMFVDLNPDSDKIIYSHFTCATDTENIRFVFAAVKDTILQ
LNLKDCGLF Sequence ID#19
hGq(ΔN-HVD-HA)-t44
 MACCLSEEAKEARRINDEIERHVRRDKRDARRELKLLLLGTGESGKSTFIKQMRIIHGSDYSDE
DKRGFTKLVYQNIFTAMQAMIRAMDTLKIPYKYEHNKAHAQLVREVDVEKVSAFDVPDYAAIKSLWNDPG
IQECYDRRREYQLSDSTKYYLNDLDRVADPAYLPTQQDVLRVRVPTTGIIEYPFDLQSVIFRMVDVGGQR
SERRKWIHCFENVTSIMFLVALSEYDQVLVESDNENRMEESKALFRTIITYPWFQNSSVILFLNKKDLLE
EKIMYSHLVDYFPEYDGPQRDAQAAREFILKMFVDNMRRDVKEIYSHMTCATDTQNVKFVFDAVTDIIIK
ENLKDCGLF Sequence ID#20
hGq(D-HA)
MTLESIMACCLSEEAKEARRINDEIERQLRRDKRDARRELKLLLLGTGESGKSTFIKQMRIIHGSDYSDE
DKRGFTKLVYQNIFTAMQAMIRAMDTLKIPYKYEHNKAHAQLVREVDVEKVSAFDVPDYAAIKSLWNDPG
IQECYDRRREYQLSDSTKYYLNDLDRVADPAYLPTQQDVLRVRVPTTGIIEYPFDLQSVIFRMVDVGGQR
SERRKWIHCFENVTSIMFLVALSEYDQVLVESDNENRMEESKALFRTIITYPWFQNSSVILFLNKKDLLE
EKIMYSHLVDYFPEYDGPQRDAQAAREFILKMFVDLNPDSDKIIYSHFTCATDTENIRFVFAAVKDTILQ
LNLKEYNLV Sequence ID#21
hGq(HVD-HA)
MTLESIMACCLSEEAKEARRINDEIERHVRRDKRDARRELKLLLLGTGESGKSTFIKQMRIIHGSDYSDE
DKRGFTKLVYQNIFTAMQAMIRAMDTLKIPYKYEHNKAHAQLVREVDVEKVSAFDVPDYAAIKSLWNDPG
IQECYDRRREYQLSDSTKYYLNDLDRVADPAYLPTQQDVLRVRVPTTGIIEYPFDLQSVIFRMVDVGGQR
SERRKWIHCFENVTSIMFLVALSEYDQVLVESDNENRMEESKALFRTIITYPWFQNSSVILFLNKKDLLE
EKIMYSHLVDYFPEYDGPQRDAQAAREFILKMFVDLNPDSDKIIYSHFTCATDTENIRFVFAAVKDTILQ
LNLKEYNLV Sequence ID#22
hGq(HVG-HA)-t5

FIGURE 4B

MTLESIMACCLSEEAKEARRINDEIERHVRRDKRDARRELKLLLLGTGESGKSTFIKQMRIIHGSGYSDE
DKRGFTKLVYQNIFTAMQAMIRAMDTLKIPYKYEHNKAHAQLVREVDVEKVSAFDVPDYAAIKSLWNDPG
IQECYDRRREYQLSDSTKYYLNDLDRVADPAYLPTQQDVLRVRVPTTGIIEYPFDLQSVIFRMVDVGGQR
SERRKWIHCFENVTSIMFLVALSEYDQVLVESDNENRMEESKALFRTIITYPWFQNSSVILFLNKKDLLE
EKIMYSHLVDYFPEYDGPQRDAQAAREFILKMFVDLNPDSDKIIYSHFTCATDTENIRFVFAAVKDTILQ
LNLKDCGLF

Sequence ID#23 hGq(HVD-HA)-t5

MTLESIMACCLSEEAKEARRINDEIERHVRRDKRDARRELKLLLLGTGESGKSTFIKQMRIIHGSDYSDE
DKRGFTKLVYQNIFTAMQAMIRAMDTLKIPYKYEHNKAHAQLVREVDVEKVSAFDVPDYAAIKSLWNDPG
IQECYDRRREYQLSDSTKYYLNDLDRVADPAYLPTQQDVLRVRVPTTGIIEYPFDLQSVIFRMVDVGGQR
SERRKWIHCFENVTSIMFLVALSEYDQVLVESDNENRMEESKALFRTIITYPWFQNSSVILFLNKKDLLE
EKIMYSHLVDYFPEYDGPQRDAQAAREFILKMFVDLNPDSDKIIYSHFTCATDTENIRFVFAAVKDTILQ
LNLKDCGLF

Sequence ID#24 hGq(ΔN-HVD-HA)-olf5

MACCLSEEAKEARRINDEIERHVRRDKRDARRELKLLLLGTGESGKSTFIKQMRIIHGSDYSDE
DKRGFTKLVYQNIFTAMQAMIRAMDTLKIPYKYEHNKAHAQLVREVDVEKVSAFDVPDYAAIKSLWNDPG
IQECYDRRREYQLSDSTKYYLNDLDRVADPAYLPTQQDVLRVRVPTTGIIEYPFDLQSVIFRMVDVGGQR
SERRKWIHCFENVTSIMFLVALSEYDQVLVESDNENRMEESKALFRTIITYPWFQNSSVILFLNKKDLLE
EKIMYSHLVDYFPEYDGPQRDAQAAREFILKMFVDLNPDSDKIIYSHFTCATDTENIRFVFAAVKDTILQ
LNLKQYELL

Sequence ID#25 hGq(HVG-HA)-t5

MTLESIMACCLSEEAKEARRINDEIERHVRRDKRDARRELKLLLLGTGESGKSTFIKQMRIIHGSGYSDE
DKRGFTKLVYQNIFTAMQAMIRAMDTLKIPYKYEHNKAHAQLVREVDVEKVSAFDVPDYAAIKSLWNDPG
IQECYDRRREYQLSDSTKYYLNDLDRVADPAYLPTQQDVLRVRVPTTGIIEYPFDLQSVIFRMVDVGGQR
SERRKWIHCFENVTSIMFLVALSEYDQVLVESDNENRMEESKALFRTIITYPWFQNSSVILFLNKKDLLE
EKIMYSHLVDYFPEYDGPQRDAQAAREFILKMFVDLNPDSDKIIYSHFTCATDTENIRFVFAAVKDTILQ
LNLKQYELL

Sequence ID#26 hGq(HVD-HA)-t5

MTLESIMACCLSEEAKEARRINDEIERHVRRDKRDARRELKLLLLGTGESGKSTFIKQMRIIHGSDYSDE
DKRGFTKLVYQNIFTAMQAMIRAMDTLKIPYKYEHNKAHAQLVREVDVEKVSAFDVPDYAAIKSLWNDPG
IQECYDRRREYQLSDSTKYYLNDLDRVADPAYLPTQQDVLRVRVPTTGIIEYPFDLQSVIFRMVDVGGQR
SERRKWIHCFENVTSIMFLVALSEYDQVLVESDNENRMEESKALFRTIITYPWFQNSSVILFLNKKDLLE
EKIMYSHLVDYFPEYDGPQRDAQAAREFILKMFVDLNPDSDKIIYSHFTCATDTENIRFVFAAVKDTILQ
LNLKQYELL

$G\alpha_Q$ PROTEIN VARIANTS AND THEIR USE IN THE ANALYSIS AND DISCOVERY OF AGONISTS AND ANTAGONISTS OF CHEMOSENSORY RECEPTORS

CROSS-REFERENCE TO RELATED APPLICATIONS

This application claims priority to U.S. Provisional Application No. 60/243,770, filed on Oct. 30, 2000, and is incorporated herein by reference in its entirety.

FIELD OF INVENTION

This invention relates to Gαq protein variants and their use in the analysis and discovery of agonists and antagonists of chemosensory receptors, such as G protein coupled receptors involved in sensing of tastants, olfactants, and pheromones.

BACKGROUND OF INVENTION

Heterotrimeric G proteins, consisting of alpha, beta and gamma subunits, couple ligand-bound seven transmembrane domain receptors (GPCRs or G-protein coupled receptors) to the regulation of effector proteins and production of intracellular second messengers such as cAMP, cGMP, and $Ca^{2+}$. G protein signaling mediates the perception of environmental cues in all higher eukaryotic organisms, including yeast, Dictyostelium, plants, and animals. Agonist-bound sensory receptors catalyze the exchange of GTP for GDP on the surface of the Gα subunit to initiate intracellular responses to extracellular signals. Intracellular signaling is mediated through various effector enzymes, including cGMP phosphodiesterase, phospholipase C, adenylate cyclase, etc. (see Kinnamon & Margolskee, 1996, Curr. Opinion Neurobiol. 6: 506-513). Most effector proteins interact with the Gα, although Gβγ subunits also contribute to the specificity of receptor-G protein coupling (Xu et al., 1998, J. Biol. Chem. 273(42): 27275-79).

The G protein α subunits are grouped into four families, $G\alpha_s$, $G\alpha_i$, $G\alpha_q$, and $G\alpha_{12}$ according to their sequence homologies and functional similarities. The $G\alpha_q$ family members couple a large group of GPCRs to phospholipase C. Activation of $G\alpha_q$ coupled GPCRs induces intracellular calcium release and the capacitative calcium entry from extracellular space. The consequential increase of cytosolic calcium concentration can be effectively detected by using synthetic or genetically-engineered fluorescent calcium indicators, bioluminescent calcium indicators, calcium-activated ion currents, and by monitoring calcium-regulated gene transcription. Assays based on such calcium readout are available in high-throughput screening (HTS) format.

Signaling specificity among α subunits of the same class having similar biochemical functions is not well understood in vivo. For instance, the $G\alpha_q$ ($G_q$) class includes four proteins expressed in mammals, called $G\alpha_q$, $G\alpha_{11}$, $G\alpha_{14}$, and $G\alpha_{15}$ (in mice, $G\alpha_{16}$ in humans). Whereas orthologs of these subunits are highly conserved across species (99, 97, 96 and 85% identity, respectively), paralogs of these subunits (expressed in the same species) are not as conserved. This suggests that each type of subunit in the $G_q$ class has a distinct function, however, when transfected into Sf9 cells, the subunits stimulated phospholipase C with similar potency and showed similar activities (Nakamura et al., 1995, J. Biol. Chem. 270: 6246-6253). Xu and colleagues subsequently showed by gene knockouts in mice that $Gq_\alpha$ subunits promiscuously couple to several different receptors in various cell types (1998, J. Biol. Chem. 273 (42): 27275).

The promiscuity of the $G\alpha_q$ subclass of G protein subunits provides a valuable tool for analyzing the role of G protein complexes and GPCRs in chemosensory transduction. For instance, the ability of $G\alpha_q$ proteins to bypass the selectivity of the receptor G-protein interaction can be used to study the molecular mechanism of receptor-induced G-protein activation. In addition, the promiscuity toward receptors may be helpful in identifying ligands corresponding to orphan receptors whose signaling properties are unknown. Promiscuous G protein subunits play a particularly useful role in generating screening assays for high affinity GPCR agonists, antagonists, and modulators of chemosensory activity, in that using a single G protein coupler removes the variability of the G protein from the equation, thereby simplifying interpretation of results gleaned from various modulating compounds and GPCRs. Chemosensory modulating compounds involved in taste and/or smell, for instance, could then be used in the pharmaceutical and food industries to customize taste or aroma. In addition, such chemosensory molecules could be used to generate topographic maps that elucidate the relationship between the taste cells of the tongue or olfactory receptors (Ors) and sensory neurons leading to the brain.

Despite their promiscuity, however, $G\alpha_q$ class subunits do not mediate all GPCR—effector interactions. For instance, human $G\alpha_{16}$ and its murine counterpart $G\alpha_{15}$ are promiscuous G proteins in that they couple to GPCRs of different G protein families (Offermanns and Simon, 1995; Negulescu et al., 1997). However, they are not true universal adapters for GPCRs in that there are at least 11 GPCRs reported to be incapable of activating Gα15/Gα16 (Wu et al., 1992; Arai et al., 1996; Kuang et al., 1996; Lee et al., 1998; Parmentier et al., 1998; Mody et al., 2000). Similar problems arise when using $G\alpha_{15}/\alpha_{16}$ to identify ligands of ORs and T2Rs (bitter taste receptors) in that (1) calcium responses to odorants are small and quickly desensitized for ORs in $G\alpha_{15}/\alpha_{16}$ transiently transfected cells (Krautwurst et al., 1998); (2) most T2Rs remain orphan using cell lines stably transfected with $G\alpha_{15}$ (Adler et al., 2000; Chandrashekar et al., 2000); and (3) threshold concentration of denatonium measured is at least one order higher than expected for bitter receptors, hT2R4 and mT2R8 expressed in cells stably transfected with $G\alpha_{15}$ (Adler et al., 2000; Chandrashekar et al., 2000). These problems suggest that the coupling efficiency between ORs/T2Rs and $G\alpha_{15}/\alpha_{16}$ is weak and may vary within the family of ORs and T2Rs.

Given the partial promiscuity of $G\alpha_q$ class proteins, it would be desirable to identify or create Gα a protein subunits that are more promiscuous than their native counterparts, and which are capable of interacting with a wider variety GPCRs.

SUMMARY OF INVENTION

The present invention addresses the above described problems associated with using $G\alpha_{15}/\alpha_{16}$, as well as other problems known in the art relating to the use of weakly promiscuous Gα proteins. Generally, the invention provides a series of $G\alpha_q$ ($G_q$ class) protein variants that functionally couple sensory cell receptors such as taste GPCRs (TRs) and olfactory GPCRs (ORs). According to the invention, the functional coupling can be determined, for example, by measuring changes in intracellular IP3 or calcium. In a particular embodiment, the $G_q$ protein variants can be expressed in mammalian cell lines or *Xenopus* oocytes, and then evaluated using calcium fluorescence imaging and electrophysiological recording.

In one aspect of the invention, G alpha class q ($G_q$) variants that are capable of widely promiscuous functional coupling to chemosensory receptors, such as taste and olfactory receptors, and isolated nucleic acid sequences encoding the same are provided. Another aspect of the invention is directed to chimeric $G_q$ variants and the isolated nucleic acids encoding the same. In one embodiment, the chimeric $G_q$ protein variants comprise C-terminal sequences from transducin or $G\alpha_{olf}$, which exhibit improved functional coupling to taste and olfactory receptors, respectively.

In yet another aspect of the invention, a method for the analysis and discovery of agonists and/or antagonists of chemosensory receptors using the $G_q$ protein variants is provided. One embodiment is directed to a mammalian cell-based assay using a transiently transfected gene or cDNA encoding a $G_q$ protein variant. Another embodiment is directed to a mammalian cell-based assay using a stably expressed gene or cDNAs encoding $G_q$ protein variants. In yet another embodiment, a method for analysis and discovery of agonists and/or antagonists of chemosensory receptors in *Xenopus* oocytes using genes, RNAs or DNAs encoding $G_q$ protein variants is provided. The agonists and/or antagonists discovered using the disclosed assays are also encompassed, as are antibodies which bind specifically to the $G_q$ variants described herein, but not those which also bind to known $G_q$ proteins.

Other aspects of the invention relate to expression vectors comprising nucleic acid sequences encoding the $G_q$ protein variants of the invention, as well as host cells comprising such expression vectors. Further aspects of the invention will become apparent to one of skill in the art from the following detailed description and examples.

BRIEF DESCRIPTION OF THE FIGURES

FIG. 1 illustrates the alignment of amino acid sequences of human $G\alpha_q$, $G\alpha_s$ and $G\alpha_{16}$ (SEQ ID NOs:37-39, respectively) by the Clustal method.

FIG. 2 illustrates the amino acid sequences of mouse (SEQ ID NO:1) and human $G\alpha_q$ (SEQ ID NO:37). Significant amino acids described herein are boxed and differences between human and mouse are underlined.

FIGS. 3A, 3B, 3C and 3D illustrate the amino acid sequences of mouse and human $G\alpha_q$ proteins according to the invention. The variations of the amino acids of $G\alpha_q$ are depicted in parenthesis. The sequence numbers of amino acid H or Q, V or L are 28 and 29 respectively. The sequence number of amino acid G or D is 66. Truncation of N-terminal amino acids (MTLESI) are shown as ΔN. Hemaglutinin (HA) epitope tag (DVPDYA) spans from 125 to 130. C-terminal five amino acids (–t5) or 44 amino acids (–t44) of transducin and five amino acids of $G\alpha_{olf}$ $_{(-olf}5$) are used respectively to replace those of $G\alpha_q$.

FIGS. 4A and 4B illustrate additional amino acid sequences according to the invention.

DETAILED DESCRIPTION OF THE INVENTION

As described above, there are known problems with the use of $G\alpha_{15}/G\alpha_{16}$ to couple chemosensory receptors in that the coupling efficiency between ORs/T2Rs and $G\alpha_{15}/\alpha_{16}$ is weak and may vary within the family of ORs and T2Rs (bitter taste receptors). As such, the invention provides a series of $G_q$ protein variants that functionally couple sensory cell receptors such as taste GPCRs (TRs) and olfactory GPCRs (ORs) in a promiscuous manner. According to the invention, "promiscuous" or "promiscuity" refers to the ability to functionally couple to more than one taste GCPRs and/or olfactory GPCRs. "Increased promiscuity" or "widely" promiscuous refers to the ability to. functionally couple to more taste GCPRs and/or olfactory GPCRs than would be demonstrated by the native $G_q$ protein.

The term "$G_q$" as used herein encompasses all the $G\alpha_q$ subclasses, including $G\alpha_q$, $G\alpha_{11}$, $G\alpha_{14}$, and $G\alpha_{15}$ (in mice, $G\alpha_{16}$ in humans). However, the chimeric promiscuous or widely promiscuous $G_q$ proteins described herein may have sequences incorporated from other Gα class proteins, for instance, from $G\alpha_s$, $G\alpha_i$ and $G\alpha_{12}$. The existing variation between members of the Gα class could be utilized in combination with the characteristic of promiscuity to generate promiscuous $G_q$ proteins having altered or new receptor specificities. Protein sequence similarity between $G\alpha_q$ and $G\alpha 15/G\alpha_q 16$ is less than 57% (FIG. 1). Accordingly, such high divergence should result in significant differences in efficiency and selectivity of receptor coupling. The identification of functionally active Gq protein variants could allow for the pharmacological and genetic modulation of sensory transduction pathways.

For example, Gq protein variants could enable screening for high affinity agonists, antagonists, inverse agonists, and other modulators of sensory cell transduction and activity. Such sensory cell modulators could then be used in the pharmaceutical and food industries to customize sensory perceptions. In addition Gq protein variants could serve as tools in the generation of sensory topographic maps.

According to the invention, Gq protein variants include variants having point mutations that increase promiscuity with regard to GPCR coupling. For instance, the inventors have found that mouse $G\alpha_q$ variants comprising a Gly to Asp change at position 66 (G66D) demonstrate increased promiscuity. Similar mutations are predicted to have a similar effect on the activity of the corresponding human $G\alpha_{16}$ subunit given the level of homology and similar activity demonstrated between the two proteins. The mutation G66D is localized at linker 1 region between helices α1 and αA of $G\alpha_q$ (Lambright et al., 1996). For reference, the amino acid sequences for mouse and human $G\alpha_q$ are listed in FIG. 2.

It was found by functional analysis using single-cell calcium imaging that activation of multi-family GPCRs evoked increases in cytosolic calcium in the presence of the $G\alpha_q$ variants with the G66D mutation. These GPCRs include $G\alpha_s$-coupled β-adrenergic receptor, $G\alpha_{olf}$-coupled mouse I7 olfactory receptor, $G\alpha_i$-coupled m2 muscarinic receptor, and gustducin-coupled bitter receptor mT2R5. No significant change in cytosolic calcium could be detected by activation of the above GPCRs in the absence of the $G\alpha_q$ variants. Additional GPCRs can include those disclosed in U.S. patent application Ser. No. 09/510,332 filed Feb. 22, 2000; and U.S. Provisional Application Nos. 60/213,849 filed Jun. 23, 2000; 60/209,840 filed Jun. 6, 2000; 60/195,536 filed Apr. 7, 2000; 60/195,534 filed Apr. 7, 2000; 60/195,532 filed Apr. 7, 2000; which are herein incorporated by references for all purposes in a manner consistent with this disclosure.

Thus, $G\alpha_q$ variants according to the invention can comprise amino acid substitutions at or near position 66, or at any other position that results in an increase of promiscuity by the variant Gα protein. Other $G_q$ subclass variants can be designed having similar mutations. Mutations can be identified and isolated using site directed or random mutagenesis according to techniques that are known in the art, including random saturation mutagenesis around the mutation sites described herein. The variants may comprise these one or more of these mutations alone or in combination with C-terminal substitutions. In another embodiment of the invention, $G\alpha_q$ and other $G_q$ subclass variants comprise C-terminal sequences derived from other G proteins.

For instance, the present inventors have also discovered that the Gly to Asp mutation is synergistic with the replacement of the C-terminus of $G\alpha_q$ by that of transducin or $G\alpha_{olf}$. $G\alpha_q$ proteins containing C-terminal amino acids from transducin or $G\alpha_{olf}$ in combination with a Gly66 to Asp alteration show increased activity compared to individual chimeras alone. A preferred embodiment is a variant $G_q$ proteins having at least about five amino acids in the C terminus of said $G_q$ protein replaced by at least about five amino acids from the C terminus of $G\alpha_{olf}$ or transducin, wherein said C-terminal substitution increases promiscuity of said variant $G_q$ protein as compared to the corresponding native $G_q$ protein. Up to 44 amino acids of the C terminus of transducin or $G\alpha_{olf}$ may be incorporated. Other possible variants are shown in FIGS. 3 and 4.

Other mutations and substitutions are envisioned to be within the scope of the invention. For instance, it would be within the level of skill in the art to perform additional amino acid substitutions at other amino acid positions using known protocols of recombinant gene technology including PCR, gene cloning, site-directed mutagenesis of cDNA, transfection of host cells, and in-vitro transcription. The variants could then be screened for functional coupling to chemosensory receptors as described herein. Further, additional C-terminal substitutions could be made from other G-protein molecules known in the art.

The present invention also includes isolated $G\alpha_q$ subunit polypeptide variants comprising polypeptides with greater than 80% amino acid sequence identity to a sequence selected from the group consisting of SEQ ID Nos 1-26. More preferably, variants comprising polypeptides with greater than 90% amino acid sequence identity are included, with the most preferable homologs being at least about 95% identical to the variants described herein.

The invention also includes isolated nucleic acid sequences encoding the $G_q$ protein variant polypeptides of the invention. Included are isolated nucleic acid sequences comprising a nucleic acid encoding a polypeptide with greater than 80% amino acid sequence identity to a sequence selected from the group consisting of SEQ ID Nos 1-26. More preferably, the isolated nucleic acid sequence encoding a $G\alpha_q$ protein variant comprises a nucleic acid encoding a polypeptide with greater than 90% amino acid sequence identity to a sequence selected from the group consisting of SEQ ID Nos 1-26. Most preferred are isolated nucleic acid sequences encoding $G\alpha_q$ protein variants which comprise a nucleic acid encoding a polypeptide with greater than about 95% amino acid sequence identity to a sequence selected from the group consisting of SEQ ID Nos 1-26.

The terms "identical" or "percent identity" in the context of two or more protein or nucleic acid sequences refers to sequences or subsequences that are the same or have a specified percentage of amino acid residues or nucleotides that are the same when compared and aligned for maximum correspondence over a comparison window or designated region, using either a sequence comparison algorithm that is known in the art or by manual inspection. Sequences with over 80% sequence identity are said to be "substantially identical." Optionally, the identity, exists over a region that is at least about 25-30 amino acids or nucleotides in length, or optionally over a region that is 75-100 amino acids or nucleotides in length.

For sequence comparison, typically one sequence acts as a reference sequence to which test sequences are compared. When using a sequence comparison algorithm, test and reference sequences are entered into a computer, subsequence coordinates are designated, if necessary, and sequence algorithm program parameters are designated. A "comparison window" as used herein includes reference to a segment of any one of the number of contiguous positions selected from the group consisting of from 25 to 500, usually about 50 to about 200, more usually about 100 to 150 in which a sequence may be compared to a reference sequence of the same number of contiguous positions after the two sequences are optimally aligned. Methods of alignment of sequences are well known in the art (see, e.g., Smith and Waterman, 1981, Adv. Appl. Math. 2: 482, Needleman and Wunsch, 1970, J. Mol. Biol. 48: 443, Pearson and Lipman, 1988, Proc. Natl. Acad. Sci. USA 85: 2444, and Current Protocols in Molecular Biology, Ausubel et al., 1995 Suppl.).

One example of a useful algorithm is PILEUP. PILEUP creates a multiple sequence alignment from a group of related sequences using progressive, pairwise alignments to show relationship and percent sequence identity, and can be obtained from the GCG sequence analysis software package, e.g., version 7.0 (Devereaux et al., 1984, Nuci. Acids Res. 12: 387-395). Another example of an algorithm that is suitable for determining percent sequence identity is the BLAST or BLAST 2.0 algorithm described in Altschul et al., 1977, Nuc. Acids Res. 25: 3389-3402 (1977) and Altschul et al., 1990, J. Mol. Biol. 215: 403-410, respectively. Software for performing BLAST analyses is publicly available through the National Center for Biotechnology Information website.

Also included in the present invention are antibodies that selectively bind to the variant $G_q$ alpha proteins described herein, but not to the corresponding native $G_q$ alpha protein. Such antibodies include whole, chimeric, humanized, tetramer, single chain, domain-deleted and other recombinant antibodies of any immunglobulin class, as well as antibody fragments, Fv, Fab', (Fab)'$_2$, etc. Preparation of such antibodies may be performed using any method known in the art (see, e.g., Kohler and Milstein, 1975, Nature 256: 495-97; Kozbar et al., 1983, Immunology Today 4: 72; Cole et al., pp. 77-96 in Monoclonal Antibodies and Cancer Therapy, 1985). Mice or other animals may be immunized with the $G_q$ protein variants of the invention in order to generate antibodies, which may be screened to identify those specific for the $G_q$ variants of the invention which also do not-recognize the corresponding native $G_q$ protein.

The present invention also encompasses expression vectors comprising the nucleic acid sequences of the present invention operably linked to a promoter that functions in mammalian cells or *Xenopus* oocytes. A "promoter" is defined as an array of nucleic acid control sequences that direct transcription of a nucleic acid. A "promoter" includes all the necessary sequences near the start site of transcription, i.e., including a polymerase binding site. A promoter optionally includes distal enhancer or repressor elements which can be located as much as thousands base pairs away from the start site of transcription. Promoters may be either constitutive, i.e. active under most environmental and developmental conditions, or inducible, i.e., under specific environmental or developmental control. The term "operably linked" refers to a functional linkage between a nucleic acid expression control sequence (such as a promoter) and a second nucleic acid sequence, such as one encoding a variant $G_q$ protein as described in the present invention, wherein the expression control sequence directs transcription of the nucleic acid corresponding to the second sequence. An "expression vector" is a nucleic acid construct comprising a coding nucleic acid sequence according to the invention operably linked to a promoter, which allows for recombinant production of the variant Gq proteins described herein. Expression vectors encompassed by the invention can be either incorporated into the genome of a host cell after transfection, or replicate extrachromosomally. Expression vectors can be either plasmids, viruses or nucleic acid fragments. Alternatively, coding sequences can be incorporated into the genome behind a native promoter, thereby creating an operable expression linkage following transfection. Host cells transfected with the expression vectors of the invention are also encompassed.

The present invention also includes methods for identifying a compound that modulates sensory signaling in sensory cells, the method comprising the steps of: (1) contacting the compound with a cell expressing the $G_q$ variant protein according to claim 1; and (2) determining the functional effect of said compound upon the $G_q$ protein variant. Typically, a cell expressing said $G_q$ variant protein is a transfected sensory cell, or other transfected cell suitable for making functional measurements of G protein activity, i.e., Xenopus oocyte. Functional effects of possible modulatory compounds may be determined by measuring changes in intracellular IP3 or $Ca^{2+}$. Functional effects may also be determined by measuring changes in the electrical activity of the cells expressing said $G_q$ variant protein or by observing modification of an intracellular effector enzyme. Possible modulatory compounds include agonists, antagonists, antibodies, small molecules and proteins.

Also included in the invention are methods for identifying a compound that interacts with the $G_q$ variant protein of claim 1, comprising the steps of (1) contacting said $G_q$ variant protein with a test compound; and (2) detecting a binding interaction between said compound and said $G_q$ protein variant. Methods of detecting the binding of $G_q$ protein variants to compounds can be performed wherein said $G_q$ variant protein is linked to solid phase, either covalently or noncovalently.

The present invention also includes an artificial array of GPCRs functionally coupled to the $G_q$ variant of claim 1, wherein said array is a model of a native arrangement of GPCRs. For instance, the native arrangement can be an arrangement of olfactory receptors (ORs) typically seen in a mammalian nose, or an arrangement of taste receptors typically seen on a mammalian tongue. Said taste receptors typically include at least one type of taste receptor selected from the group consisting of bitter, sweet, salty, unami and sour taste receptors, in light of the observations that such taste receptors are typically arranged in spatially organized manner. The artificial arrays of the present invention are useful for analyzing the response to different sensory compounds in relation to brain activity. Such arrays will be improved by the promiscuous variant $G_q$ proteins of the present invention, which will simplify interpretation of results that might normally be complicated by the requirement for different G protein subunits for every GPCR in such an array.

It is also envisioned that the $G_q$ protein variants of the invention could be used in other types of functional assays such as biochemical binding assays, enzymatic assays, other cell-based assay, as well as with in vivo systems such as transgenic mice.

The following examples serve merely to illustrate the invention, and should not be construed as limiting the scope of the invention in any way.

EXAMPLES

Initially, the $G\alpha_q$ variant protein termed mGq(ON-HVD-HA) of Seq ID#5, described in Kostenis et al. (1998), was shown to functionally couple to taste receptor mT2R5 and olfactory OR I7. Previously, it had not been known whether this protein would allow functional expression of chemosensory receptors such as taste and olfactory receptors. The response using the Kostenis et al G protein was weak. Therefore, in order to improve functional coupling a series of variants was created. The variants were chimeras between the variants of the Kostenis G protein which contained the C terminal sequences from $G\alpha_{olf}$ or transducin. Variants containing the C-terminal changes exhibited improved function. The use of C-terminal replacements in G proteins had previously been reported by Conklin (Conklin et al., 1993; Conklin et al., 1996; Coward et al., 1999) but the sequences from $G\alpha_{olf}$ or transducin had not previously been shown to function with taste or olfactory receptors.

A series of $G\alpha_q$ protein variants having the sequences listed in FIG. 3 were constructed and tested in mammalian cell-based systems and in Xenopus oocytes for functional coupling efficiency with bitter receptor mT2R5 and mouse olfactory receptor I7. As shown in Table I below, one set of G proteins function with a taste receptor and another set of G proteins function with an olfactory receptor. All active G proteins consisted of mouse sequences, however given the similarities between human and mouse $G\alpha_q$ proteins, it is anticipated that the human variants will also functionally couple with human chemosensory receptors.

TABLE I

Functional Activity of Gq Variants

| Gq Variants | Seq ID # | Functional Activity With Taste Receptor MT2R5 | Functional Activity with Olfactory Receptor ml7 |
|---|---|---|---|
| MGq | 1 | − | N/A |
| MGq(ΔN) | 2 | − | N/A |
| MGq(HA) | 3 | − | N/A |
| MGq(ΔN-HA) | 4 | − | N/A |
| MGq(ΔN-HVD-HA) | 5 | + | + |
| MGq(ΔN-HVD-HA)-t5 | 6 | ++ | N/A |
| MGq(ΔN-HVD-HA)-t44 | 7 | ++ | N/A |
| MGq(ΔN-HV-HA) | 8 | − | N/A |
| MGq(HV-HA) | 9 | − | N/A |
| MGq(D-HA) | 10 | + | N/A |
| MGq(HVD-HA) | 11 | + | N/A |
| MGq(HV-HA)-t5 | 12 | + | N/A |
| MGq(HVD-HA)-t5 | 13 | ++ | N/A |
| MGq(ΔN-HVD-HA)-olf5 | 14 | N/A | ++ |
| HGq | 15 | − | N/A |
| HGq(ΔN) | 16 | − | N/A |

+ means functionally couples with chemosensory receptor
++ means functionally couples with chemosensory receptor
− means does not functionally couple
N/A mean not tested

REFERENCES

Adler et al., 2000, "A novel family of taste receptors," Cell 100: 693-702.

Ari et al., 1996, "Differential regulation of G-protein-mediated signaling by chemokine receptors," J. Biol. Chem. 271: 21814-21819.

Bertin et al., 1994, "Cellular signaling by an antagonist-activated receptor/Gsα fusion protein,"Proc. Natl. Acad. Sci. USA 91: 8827-8831.

Chandrashekar et al., 2000, "T2Rs function as bitter taste receptors," Cell 100: 703-711.

Conklin et al., 1996, "Carboxyl-terminal mutations of Gpα and Gsα that alter the fidelity of receptor activation,"Mol. Pharm. 50: 885-90.

Coward et al., 1999, "Chimeric G proteins allow a high-throughput signaling assay of Gi-coupled receptors," Anal. Biochem. 270: 242-248.

Kostenis et al., 1998, "Functional characterization of a series of mutant G protein alphaq subunits displaying promiscuous receptor coupling properties," J. Biol. Chem. 273: 17886-17892.

Krautwurst et al., "Identification of ligands for olfactory receptors by functional expression of a receptor library," Cell 95: 917-26.

Kuang et al., 1996, "Selective G Protein Coupling to C-C Chemokine Receptors," J. Biol. Chem. 271:3975-3978.

Lambright et al., 1996, "The 2.0 A Crystal Structure of a Heterotrimeric G Protein," Nature, 379: 311-319.

Lee et al., 1998, "Differential Coupling of μδ and κK Opioid Receptors to $G_{\alpha 16}$-mediated Stimulation of Phospholipase C," J. Neurochem. 70:2203-2211.

Mody et al., 2000, "Incorporation of G-Specific Sequence at the Carboxyl Terminus Increases the Promiscuity of $G_{\alpha 16}$ toward $G_i$-coupled Receptors," Mol. Pharm., 57:13-23.

Negulescu et al., 1997, "Promiscuous G-protein Compositions and Their Use," U.S. Pat. No. 6,004,808.

Offermanns & Simon, 1995, Gα15 and Gα16 couple a wide variety of receptors to phospholipase C," J. Biol. Chem. 270:15175-15180.

Parmentier et al., 1998, The G protein-coupling Profile of Metabotropic Glutamate Receptors, as Determined with Exogenous G Proteins, is Independent of Their Ligand Recognition Domain," Mol. Pharmacol. 53:778-786.

Seifert et al., 1999, "GPCR-Gα Fusion Proteins: Molecular Analysis of Receptor-G-Protein Coupling," TIPS 20:383-389.

Wu et al., 1992, "Activation of Phospholipase C by α1-adrenergic Receptors is Mediated by the α Subunits of the Gq Family," J. Biol. Chem. 267:25798-25802.

What is claimed is:

1. A nucleic acid encoding a mutated Gq protein identical to the polypeptide contained in SEQ ID NO:1 or 37 except for the substitution of an aspartic acid residue for the glycine residue at position 66.

2. An expression vector containing a nucleic acid as set forth in claim 1.

3. A host cell containing an expression vector as set forth in claim 2.

4. The host cell of claim 3 which is a mammalian cell.

5. The host cell of claim 4 which is a HEK-293 cell.

6. A nucleic acid encoding a mutated Gq protein which is identical to the polypeptide contained in SEQ ID NO:1 except for the replacement of the last 5 amino acid residues with the 5 amino acid residues of the carboxy terminus of Golf or transducin.

7. An expression vector containing a nucleic acid as set forth in claim 6.

8. A host cell containing an expression vector as set forth in claim 7.

9. The host cell of claim 8 which is a HEK-293 cell.

10. A nucleic acid encoding a mutated Gq protein as set forth in claim 6 wherein said nucleic acid encodes a mutated Gq protein selected from the group consisting of the polypeptides contained in SEQ ID NO:6, SEQ ID NO:7, SEQ ID NO:13 and SEQ ID NO:17.

11. An expression vector containing a nucleic acid as set forth in claim 10.

12. A host cell containing an expression vector according to claim 11.

13. The host cell of claim 12 which is a HEK-293 cell.

14. A nucleic acid as set forth in claim 10 which encodes the polypeptide contained in SEQ ID NO:13.

15. An expression vector containing a nucleic acid according to claim 14.

16. A host cell containing an expression vector according to claim 15.

17. A host cell of claim 16 which is a HEK-293 cell.

* * * * *

SEQUENCE LISTING

<160> NUMBER OF SEQ ID NOS: 42

<210> SEQ ID NO 1
<211> LENGTH: 359
<212> TYPE: PRT
<213> ORGANISM: Mus sp.

<400> SEQUENCE: 1

```
Met Thr Leu Glu Ser Ile Met Ala Cys Cys Leu Ser Glu Glu Ala Lys
  1               5                  10                  15

Glu Ala Arg Arg Ile Asn Asp Glu Ile Glu Arg Gln Leu Arg Arg Asp
             20                  25                  30

Lys Arg Asp Ala Arg Arg Glu Leu Lys Leu Leu Leu Leu Gly Thr Gly
         35                  40                  45

Glu Ser Gly Lys Ser Thr Phe Ile Lys Gln Met Arg Ile Ile His Gly
     50                  55                  60

Ser Gly Tyr Ser Asp Glu Asp Lys Arg Gly Phe Thr Lys Leu Val Tyr
 65                  70                  75                  80

Gln Asn Ile Phe Thr Ala Met Gln Ala Met Ile Arg Ala Met Asp Thr
                 85                  90                  95

Leu Lys Ile Pro Tyr Lys Tyr Glu His Asn Lys Ala His Ala Gln Leu
            100                 105                 110

Val Arg Glu Val Asp Val Glu Lys Val Ser Ala Phe Glu Asn Pro Tyr
        115                 120                 125

Val Asp Ala Ile Lys Ser Leu Trp Asn Asp Pro Gly Ile Gln Glu Cys
    130                 135                 140

Tyr Asp Arg Arg Arg Glu Tyr Gln Leu Ser Asp Ser Thr Lys Tyr Tyr
145                 150                 155                 160

Leu Asn Asp Leu Asp Arg Val Ala Asp Pro Ser Tyr Leu Pro Thr Gln
                165                 170                 175

Gln Asp Val Leu Arg Val Arg Val Pro Thr Thr Gly Ile Ile Glu Tyr
            180                 185                 190
```

-continued

Pro Phe Asp Leu Gln Ser Val Ile Phe Arg Met Val Asp Val Gly Gly
            195                 200                 205

Gln Arg Ser Glu Arg Arg Lys Trp Ile His Cys Phe Glu Asn Val Thr
        210                 215                 220

Ser Ile Met Phe Leu Val Ala Leu Ser Glu Tyr Asp Gln Val Leu Val
225                 230                 235                 240

Glu Ser Asp Asn Glu Asn Arg Met Glu Glu Ser Lys Ala Leu Phe Arg
                245                 250                 255

Thr Ile Ile Thr Tyr Pro Trp Phe Gln Asn Ser Ser Val Ile Leu Phe
            260                 265                 270

Leu Asn Lys Lys Asp Leu Leu Glu Glu Lys Ile Met Tyr Ser His Leu
        275                 280                 285

Val Asp Tyr Phe Pro Glu Tyr Asp Gly Pro Gln Arg Asp Ala Gln Ala
290                 295                 300

Ala Arg Glu Phe Ile Leu Lys Met Phe Val Asp Leu Asn Pro Asp Ser
305                 310                 315                 320

Asp Lys Ile Ile Tyr Ser His Phe Thr Cys Ala Thr Asp Thr Glu Asn
                325                 330                 335

Ile Arg Phe Val Phe Ala Ala Val Lys Asp Thr Ile Leu Gln Leu Asn
            340                 345                 350

Leu Lys Glu Tyr Asn Leu Val
        355

<210> SEQ ID NO 2
<211> LENGTH: 353
<212> TYPE: PRT
<213> ORGANISM: Mus sp.

<400> SEQUENCE: 2

Met Ala Cys Cys Leu Ser Glu Glu Ala Lys Glu Ala Arg Arg Ile Asn
1               5                   10                  15

Asp Glu Ile Glu Arg Gln Leu Arg Arg Asp Lys Arg Asp Ala Arg Arg
                20                  25                  30

Glu Leu Lys Leu Leu Leu Leu Gly Thr Gly Glu Ser Gly Lys Ser Thr
            35                  40                  45

Phe Ile Lys Gln Met Arg Ile Ile His Gly Ser Gly Tyr Ser Asp Glu
        50                  55                  60

Asp Lys Arg Gly Phe Thr Lys Leu Val Tyr Gln Asn Ile Phe Thr Ala
65                  70                  75                  80

Met Gln Ala Met Ile Arg Ala Met Asp Thr Leu Lys Ile Pro Tyr Lys
                85                  90                  95

Tyr Glu His Asn Lys Ala His Ala Gln Leu Val Arg Glu Val Asp Val
            100                 105                 110

Glu Lys Val Ser Ala Phe Glu Asn Pro Tyr Val Asp Ala Ile Lys Ser
        115                 120                 125

Leu Trp Asn Asp Pro Gly Ile Gln Glu Cys Tyr Asp Arg Arg Arg Glu
    130                 135                 140

Tyr Gln Leu Ser Asp Ser Thr Lys Tyr Tyr Leu Asn Asp Leu Asp Arg
145                 150                 155                 160

Val Ala Asp Pro Ser Tyr Leu Pro Thr Gln Gln Asp Val Leu Arg Val
                165                 170                 175

Arg Val Pro Thr Thr Gly Ile Ile Glu Tyr Pro Phe Asp Leu Gln Ser
            180                 185                 190

Val Ile Phe Arg Met Val Asp Val Gly Gly Gln Arg Ser Glu Arg Arg

-continued

```
                195                 200                 205
Lys Trp Ile His Cys Phe Glu Asn Val Thr Ser Ile Met Phe Leu Val
    210                 215                 220
Ala Leu Ser Glu Tyr Asp Gln Val Leu Val Glu Ser Asp Asn Glu Asn
225                 230                 235                 240
Arg Met Glu Glu Ser Lys Ala Leu Phe Arg Thr Ile Thr Tyr Pro
                245                 250                 255
Trp Phe Gln Asn Ser Ser Val Ile Leu Phe Leu Asn Lys Lys Asp Leu
                260                 265                 270
Leu Glu Glu Lys Ile Met Tyr Ser His Leu Val Asp Tyr Phe Pro Glu
            275                 280                 285
Tyr Asp Gly Pro Gln Arg Asp Ala Gln Ala Ala Arg Glu Phe Ile Leu
    290                 295                 300
Lys Met Phe Val Asp Leu Asn Pro Asp Ser Asp Lys Ile Ile Tyr Ser
305                 310                 315                 320
His Phe Thr Cys Ala Thr Asp Thr Glu Asn Ile Arg Phe Val Phe Ala
                325                 330                 335
Ala Val Lys Asp Thr Ile Leu Gln Leu Asn Leu Lys Glu Tyr Asn Leu
            340                 345                 350
Val

<210> SEQ ID NO 3
<211> LENGTH: 359
<212> TYPE: PRT
<213> ORGANISM: Mus sp.

<400> SEQUENCE: 3

Met Thr Leu Glu Ser Ile Met Ala Cys Cys Leu Ser Glu Glu Ala Lys
  1               5                  10                  15
Glu Ala Arg Arg Ile Asn Asp Glu Ile Glu Arg Gln Leu Arg Arg Asp
                20                  25                  30
Lys Arg Asp Ala Arg Arg Glu Leu Lys Leu Leu Leu Leu Gly Thr Gly
            35                  40                  45
Glu Ser Gly Lys Ser Thr Phe Ile Lys Gln Met Arg Ile Ile His Gly
    50                  55                  60
Ser Gly Tyr Ser Asp Glu Asp Lys Arg Gly Phe Thr Lys Leu Val Tyr
65                  70                  75                  80
Gln Asn Ile Phe Thr Ala Met Gln Ala Met Ile Arg Ala Met Asp Thr
                85                  90                  95
Leu Lys Ile Pro Tyr Lys Tyr Glu His Asn Lys Ala His Ala Gln Leu
                100                 105                 110
Val Arg Glu Val Asp Val Glu Lys Val Ser Ala Phe Asp Val Pro Asp
            115                 120                 125
Tyr Ala Ala Ile Lys Ser Leu Trp Asn Asp Pro Gly Ile Gln Glu Cys
    130                 135                 140
Tyr Asp Arg Arg Arg Glu Tyr Gln Leu Ser Asp Ser Thr Lys Tyr Tyr
145                 150                 155                 160
Leu Asn Asp Leu Asp Arg Val Ala Asp Pro Ser Tyr Leu Pro Thr Gln
                165                 170                 175
Gln Asp Val Leu Arg Val Arg Val Pro Thr Thr Gly Ile Ile Glu Tyr
            180                 185                 190
Pro Phe Asp Leu Gln Ser Val Ile Phe Arg Met Val Asp Val Gly Gly
    195                 200                 205
Gln Arg Ser Glu Arg Arg Lys Trp Ile His Cys Phe Glu Asn Val Thr
```

-continued

```
            210                 215                 220
Ser Ile Met Phe Leu Val Ala Leu Ser Glu Tyr Asp Gln Val Leu Val
225                 230                 235                 240

Glu Ser Asp Asn Glu Asn Arg Met Glu Glu Ser Lys Ala Leu Phe Arg
                245                 250                 255

Thr Ile Ile Thr Tyr Pro Trp Phe Gln Asn Ser Ser Val Ile Leu Phe
                260                 265                 270

Leu Asn Lys Lys Asp Leu Leu Glu Glu Lys Ile Met Tyr Ser His Leu
            275                 280                 285

Val Asp Tyr Phe Pro Glu Tyr Asp Gly Pro Gln Arg Asp Ala Gln Ala
        290                 295                 300

Ala Arg Glu Phe Ile Leu Lys Met Phe Val Asp Leu Asn Pro Asp Ser
305                 310                 315                 320

Asp Lys Ile Ile Tyr Ser His Phe Thr Cys Ala Thr Asp Thr Glu Asn
                325                 330                 335

Ile Arg Phe Val Phe Ala Ala Val Lys Asp Thr Ile Leu Gln Leu Asn
                340                 345                 350

Leu Lys Glu Tyr Asn Leu Val
            355
```

<210> SEQ ID NO 4
<211> LENGTH: 353
<212> TYPE: PRT
<213> ORGANISM: Mus sp.

<400> SEQUENCE: 4

```
Met Ala Cys Cys Leu Ser Glu Glu Ala Lys Glu Ala Arg Arg Ile Asn
1               5                   10                  15

Asp Glu Ile Glu Arg Gln Leu Arg Arg Asp Lys Arg Asp Ala Arg Arg
                20                  25                  30

Glu Leu Lys Leu Leu Leu Leu Gly Thr Gly Glu Ser Gly Lys Ser Thr
            35                  40                  45

Phe Ile Lys Gln Met Arg Ile Ile His Gly Ser Gly Tyr Ser Asp Glu
        50                  55                  60

Asp Lys Arg Gly Phe Thr Lys Leu Val Tyr Gln Asn Ile Phe Thr Ala
65                  70                  75                  80

Met Gln Ala Met Ile Arg Ala Met Asp Thr Leu Lys Ile Pro Tyr Lys
                85                  90                  95

Tyr Glu His Asn Lys Ala His Ala Gln Leu Val Arg Glu Val Asp Val
                100                 105                 110

Glu Lys Val Ser Ala Phe Asp Val Pro Asp Tyr Ala Ala Ile Lys Ser
            115                 120                 125

Leu Trp Asn Asp Pro Gly Ile Gln Glu Cys Tyr Asp Arg Arg Arg Glu
        130                 135                 140

Tyr Gln Leu Ser Asp Ser Thr Lys Tyr Tyr Leu Asn Asp Leu Asp Arg
145                 150                 155                 160

Val Ala Asp Pro Ser Tyr Leu Pro Thr Gln Gln Asp Val Leu Arg Val
                165                 170                 175

Arg Val Pro Thr Thr Gly Ile Ile Glu Tyr Pro Phe Asp Leu Gln Ser
                180                 185                 190

Val Ile Phe Arg Met Val Asp Val Gly Gly Gln Arg Ser Glu Arg Arg
            195                 200                 205

Lys Trp Ile His Cys Phe Glu Asn Val Thr Ser Ile Met Phe Leu Val
        210                 215                 220
```

```
Ala Leu Ser Glu Tyr Asp Gln Val Leu Val Glu Ser Asp Asn Glu Asn
225                 230                 235                 240

Arg Met Glu Glu Ser Lys Ala Leu Phe Arg Thr Ile Ile Thr Tyr Pro
                245                 250                 255

Trp Phe Gln Asn Ser Ser Val Ile Leu Phe Leu Asn Lys Lys Asp Leu
            260                 265                 270

Leu Glu Glu Lys Ile Met Tyr Ser His Leu Val Asp Tyr Phe Pro Glu
        275                 280                 285

Tyr Asp Gly Pro Gln Arg Asp Ala Gln Ala Ala Arg Glu Phe Ile Leu
290                 295                 300

Lys Met Phe Val Asp Leu Asn Pro Asp Ser Asp Lys Ile Ile Tyr Ser
305                 310                 315                 320

His Phe Thr Cys Ala Thr Asp Thr Glu Asn Ile Arg Phe Val Phe Ala
                325                 330                 335

Ala Val Lys Asp Thr Ile Leu Gln Leu Asn Leu Lys Glu Tyr Asn Leu
            340                 345                 350

Val

<210> SEQ ID NO 5
<211> LENGTH: 353
<212> TYPE: PRT
<213> ORGANISM: Mus sp.

<400> SEQUENCE: 5

Met Ala Cys Cys Leu Ser Glu Glu Ala Lys Glu Ala Arg Arg Ile Asn
1               5                   10                  15

Asp Glu Ile Glu Arg His Val Arg Arg Asp Lys Arg Asp Ala Arg Arg
            20                  25                  30

Glu Leu Lys Leu Leu Leu Leu Gly Thr Gly Glu Ser Gly Lys Ser Thr
        35                  40                  45

Phe Ile Lys Gln Met Arg Ile Ile His Gly Ser Asp Tyr Ser Asp Glu
    50                  55                  60

Asp Lys Arg Gly Phe Thr Lys Leu Val Tyr Gln Asn Ile Phe Thr Ala
65                  70                  75                  80

Met Gln Ala Met Ile Arg Ala Met Asp Thr Leu Lys Ile Pro Tyr Lys
                85                  90                  95

Tyr Glu His Asn Lys Ala His Ala Gln Leu Val Arg Glu Val Asp Val
            100                 105                 110

Glu Lys Val Ser Ala Phe Asp Val Pro Asp Tyr Ala Ala Ile Lys Ser
        115                 120                 125

Leu Trp Asn Asp Pro Gly Ile Gln Glu Cys Tyr Asp Arg Arg Arg Glu
    130                 135                 140

Tyr Gln Leu Ser Asp Ser Thr Lys Tyr Tyr Leu Asn Asp Leu Asp Arg
145                 150                 155                 160

Val Ala Asp Pro Ser Tyr Leu Pro Thr Gln Gln Asp Val Leu Arg Val
                165                 170                 175

Arg Val Pro Thr Thr Gly Ile Ile Glu Tyr Pro Phe Asp Leu Gln Ser
            180                 185                 190

Val Ile Phe Arg Met Val Asp Val Gly Gly Gln Arg Ser Glu Arg Arg
        195                 200                 205

Lys Trp Ile His Cys Phe Glu Asn Val Thr Ser Ile Met Phe Leu Val
    210                 215                 220

Ala Leu Ser Glu Tyr Asp Gln Val Leu Val Glu Ser Asp Asn Glu Asn
225                 230                 235                 240
```

```
Arg Met Glu Glu Ser Lys Ala Leu Phe Arg Thr Ile Ile Thr Tyr Pro
                245                 250                 255

Trp Phe Gln Asn Ser Ser Val Ile Leu Phe Leu Asn Lys Lys Asp Leu
            260                 265                 270

Leu Glu Glu Lys Ile Met Tyr Ser His Leu Val Asp Tyr Phe Pro Glu
            275                 280                 285

Tyr Asp Gly Pro Gln Arg Asp Ala Gln Ala Ala Arg Glu Phe Ile Leu
            290                 295                 300

Lys Met Phe Val Asp Leu Asn Pro Asp Ser Asp Lys Ile Ile Tyr Ser
305                 310                 315                 320

His Phe Thr Cys Ala Thr Asp Thr Glu Asn Ile Arg Phe Val Phe Ala
                325                 330                 335

Ala Val Lys Asp Thr Ile Leu Gln Leu Asn Leu Lys Glu Tyr Asn Leu
            340                 345                 350

Val

<210> SEQ ID NO 6
<211> LENGTH: 353
<212> TYPE: PRT
<213> ORGANISM: Mus sp.

<400> SEQUENCE: 6

Met Ala Cys Cys Leu Ser Glu Glu Ala Lys Glu Ala Arg Arg Ile Asn
1               5                   10                  15

Asp Glu Ile Glu Arg His Val Arg Arg Asp Lys Arg Asp Ala Arg Arg
            20                  25                  30

Glu Leu Lys Leu Leu Leu Leu Gly Thr Gly Glu Ser Gly Lys Ser Thr
        35                  40                  45

Phe Ile Lys Gln Met Arg Ile Ile His Gly Ser Asp Tyr Ser Asp Glu
    50                  55                  60

Asp Lys Arg Gly Phe Thr Lys Leu Val Tyr Gln Asn Ile Phe Thr Ala
65                  70                  75                  80

Met Gln Ala Met Ile Arg Ala Met Asp Thr Leu Lys Ile Pro Tyr Lys
                85                  90                  95

Tyr Glu His Asn Lys Ala His Ala Gln Leu Val Arg Glu Val Asp Val
            100                 105                 110

Glu Lys Val Ser Ala Phe Asp Val Pro Asp Tyr Ala Ala Ile Lys Ser
        115                 120                 125

Leu Trp Asn Asp Pro Gly Ile Gln Glu Cys Tyr Asp Arg Arg Arg Glu
    130                 135                 140

Tyr Gln Leu Ser Asp Ser Thr Lys Tyr Tyr Leu Asn Asp Leu Asp Arg
145                 150                 155                 160

Val Ala Asp Pro Ser Tyr Leu Pro Thr Gln Gln Asp Val Leu Arg Val
                165                 170                 175

Arg Val Pro Thr Thr Gly Ile Ile Glu Tyr Pro Phe Asp Leu Gln Ser
            180                 185                 190

Val Ile Phe Arg Met Val Asp Val Gly Gly Gln Arg Ser Glu Arg Arg
        195                 200                 205

Lys Trp Ile His Cys Phe Glu Asn Val Thr Ser Ile Met Phe Leu Val
    210                 215                 220

Ala Leu Ser Glu Tyr Asp Gln Val Leu Val Glu Ser Asp Asn Glu Asn
225                 230                 235                 240

Arg Met Glu Glu Ser Lys Ala Leu Phe Arg Thr Ile Ile Thr Tyr Pro
                245                 250                 255
```

-continued

```
Trp Phe Gln Asn Ser Ser Val Ile Leu Phe Leu Asn Lys Lys Asp Leu
            260                 265                 270

Leu Glu Glu Lys Ile Met Tyr Ser His Leu Val Asp Tyr Phe Pro Glu
        275                 280                 285

Tyr Asp Gly Pro Gln Arg Asp Ala Gln Ala Ala Arg Glu Phe Ile Leu
290                 295                 300

Lys Met Phe Val Asp Leu Asn Pro Asp Ser Asp Lys Ile Ile Tyr Ser
305                 310                 315                 320

His Phe Thr Cys Ala Thr Asp Thr Glu Asn Ile Arg Phe Val Phe Ala
                325                 330                 335

Ala Val Lys Asp Thr Ile Leu Gln Leu Asn Leu Lys Asp Cys Gly Leu
                340                 345                 350

Phe
```

<210> SEQ ID NO 7
<211> LENGTH: 353
<212> TYPE: PRT
<213> ORGANISM: Mus sp.

<400> SEQUENCE: 7

```
Met Ala Cys Cys Leu Ser Glu Glu Ala Lys Glu Ala Arg Arg Ile Asn
1               5                   10                  15

Asp Glu Ile Glu Arg His Val Arg Arg Asp Lys Arg Asp Ala Arg Arg
            20                  25                  30

Glu Leu Lys Leu Leu Leu Leu Gly Thr Gly Glu Ser Gly Lys Ser Thr
        35                  40                  45

Phe Ile Lys Gln Met Arg Ile Ile His Gly Ser Asp Tyr Ser Asp Glu
    50                  55                  60

Asp Lys Arg Gly Phe Thr Lys Leu Val Tyr Gln Asn Ile Phe Thr Ala
65                  70                  75                  80

Met Gln Ala Met Ile Arg Ala Met Asp Thr Leu Lys Ile Pro Tyr Lys
                85                  90                  95

Tyr Glu His Asn Lys Ala His Ala Gln Leu Val Arg Glu Val Asp Val
            100                 105                 110

Glu Lys Val Ser Ala Phe Asp Val Pro Asp Tyr Ala Ala Ile Lys Ser
        115                 120                 125

Leu Trp Asn Asp Pro Gly Ile Gln Glu Cys Tyr Asp Arg Arg Arg Glu
    130                 135                 140

Tyr Gln Leu Ser Asp Ser Thr Lys Tyr Tyr Leu Asn Asp Leu Asp Arg
145                 150                 155                 160

Val Ala Asp Pro Ser Tyr Leu Pro Thr Gln Gln Asp Val Leu Arg Val
                165                 170                 175

Arg Val Pro Thr Thr Gly Ile Ile Glu Tyr Pro Phe Asp Leu Gln Ser
            180                 185                 190

Val Ile Phe Arg Met Val Asp Val Gly Gly Gln Arg Ser Glu Arg Arg
        195                 200                 205

Lys Trp Ile His Cys Phe Glu Asn Val Thr Ser Ile Met Phe Leu Val
    210                 215                 220

Ala Leu Ser Glu Tyr Asp Gln Val Leu Val Glu Ser Asp Asn Glu Asn
225                 230                 235                 240

Arg Met Glu Glu Ser Lys Ala Leu Phe Arg Thr Ile Ile Thr Tyr Pro
                245                 250                 255

Trp Phe Gln Asn Ser Ser Val Ile Leu Phe Leu Asn Lys Lys Asp Leu
            260                 265                 270
```

```
Leu Glu Glu Lys Ile Met Tyr Ser His Leu Val Asp Tyr Phe Pro Glu
            275                 280                 285

Tyr Asp Gly Pro Gln Arg Asp Ala Gln Ala Ala Arg Glu Phe Ile Leu
        290                 295                 300

Lys Met Phe Val Asp Asn Met Arg Arg Asp Val Lys Glu Ile Tyr Ser
305                 310                 315                 320

His Met Thr Cys Ala Thr Asp Thr Gln Asn Val Lys Phe Val Phe Asp
                325                 330                 335

Ala Val Thr Asp Ile Ile Ile Lys Glu Asn Leu Lys Asp Cys Gly Leu
                340                 345                 350

Phe

<210> SEQ ID NO 8
<211> LENGTH: 353
<212> TYPE: PRT
<213> ORGANISM: Mus sp.

<400> SEQUENCE: 8

Met Ala Cys Cys Leu Ser Glu Glu Ala Lys Glu Ala Arg Arg Ile Asn
  1               5                  10                  15

Asp Glu Ile Glu Arg His Val Arg Arg Asp Lys Arg Asp Ala Arg Arg
             20                  25                  30

Glu Leu Lys Leu Leu Leu Leu Gly Thr Gly Glu Ser Gly Lys Ser Thr
         35                  40                  45

Phe Ile Lys Gln Met Arg Ile Ile His Gly Ser Gly Tyr Ser Asp Glu
     50                  55                  60

Asp Lys Arg Gly Phe Thr Lys Leu Val Tyr Gln Asn Ile Phe Thr Ala
 65                  70                  75                  80

Met Gln Ala Met Ile Arg Ala Met Asp Thr Leu Lys Ile Pro Tyr Lys
                 85                  90                  95

Tyr Glu His Asn Lys Ala His Ala Gln Leu Val Arg Glu Val Asp Val
            100                 105                 110

Glu Lys Val Ser Ala Phe Asp Val Pro Asp Tyr Ala Ala Ile Lys Ser
        115                 120                 125

Leu Trp Asn Asp Pro Gly Ile Gln Glu Cys Tyr Asp Arg Arg Arg Glu
130                 135                 140

Tyr Gln Leu Ser Asp Ser Thr Lys Tyr Tyr Leu Asn Asp Leu Asp Arg
145                 150                 155                 160

Val Ala Asp Pro Ser Tyr Leu Pro Thr Gln Gln Asp Val Leu Arg Val
                165                 170                 175

Arg Val Pro Thr Thr Gly Ile Ile Glu Tyr Pro Phe Asp Leu Gln Ser
            180                 185                 190

Val Ile Phe Arg Met Val Asp Val Gly Gly Gln Arg Ser Glu Arg Arg
        195                 200                 205

Lys Trp Ile His Cys Phe Glu Asn Val Thr Ser Ile Met Phe Leu Val
    210                 215                 220

Ala Leu Ser Glu Tyr Asp Gln Val Leu Val Glu Ser Asp Asn Glu Asn
225                 230                 235                 240

Arg Met Glu Glu Ser Lys Ala Leu Phe Arg Thr Ile Ile Thr Tyr Pro
                245                 250                 255

Trp Phe Gln Asn Ser Ser Val Ile Leu Phe Leu Asn Lys Lys Asp Leu
            260                 265                 270

Leu Glu Glu Lys Ile Met Tyr Ser His Leu Val Asp Tyr Phe Pro Glu
        275                 280                 285
```

-continued

```
Tyr Asp Gly Pro Gln Arg Asp Ala Gln Ala Arg Glu Phe Ile Leu
        290                 295                 300
Lys Met Phe Val Asp Leu Asn Pro Asp Ser Asp Lys Ile Ile Tyr Ser
305                 310                 315                 320
His Phe Thr Cys Ala Thr Asp Thr Glu Asn Ile Arg Phe Val Phe Ala
                325                 330                 335
Ala Val Lys Asp Thr Ile Leu Gln Leu Asn Leu Lys Glu Tyr Asn Leu
            340                 345                 350
Val
```

<210> SEQ ID NO 9
<211> LENGTH: 359
<212> TYPE: PRT
<213> ORGANISM: Mus sp.

<400> SEQUENCE: 9

```
Met Thr Leu Glu Ser Ile Met Ala Cys Cys Leu Ser Glu Glu Ala Lys
  1               5                  10                  15
Glu Ala Arg Arg Ile Asn Asp Glu Ile Glu Arg His Val Arg Arg Asp
             20                  25                  30
Lys Arg Asp Ala Arg Arg Glu Leu Lys Leu Leu Leu Leu Gly Thr Gly
         35                  40                  45
Glu Ser Gly Lys Ser Thr Phe Ile Lys Gln Met Arg Ile Ile His Gly
     50                  55                  60
Ser Gly Tyr Ser Asp Glu Asp Lys Arg Gly Phe Thr Lys Leu Val Tyr
 65                  70                  75                  80
Gln Asn Ile Phe Thr Ala Met Gln Ala Met Ile Arg Ala Met Asp Thr
                 85                  90                  95
Leu Lys Ile Pro Tyr Lys Tyr Glu His Asn Lys Ala His Ala Gln Leu
            100                 105                 110
Val Arg Glu Val Asp Val Glu Lys Val Ser Ala Phe Asp Val Pro Asp
        115                 120                 125
Tyr Ala Ala Ile Lys Ser Leu Trp Asn Asp Pro Gly Ile Gln Glu Cys
    130                 135                 140
9Tyr Asp Arg Arg Arg Glu Tyr Gln Leu Ser Asp Ser Thr Lys Tyr Tyr
145                 150                 155                 160
L
eu Asn Asp Leu Asp Arg Val Ala Asp Pro Ser Tyr Leu Pro Thr Gln
                165                 170                 175
Gln Asp Val Leu Arg Val Arg Val Pro Thr Thr Gly Ile Ile Glu Tyr
            180                 185                 190
Pro Phe Asp Leu Gln Ser Val Ile Phe Arg Met Val Asp Val Gly Gly
        195                 200                 205
Gln Arg Ser Glu Arg Arg Lys Trp Ile His Cys Phe Glu Asn Val Thr
    210                 215                 220
Ser Ile Met Phe Leu Val Ala Leu Ser Glu Tyr Asp Gln Val Leu Val
225                 230                 235                 240
Glu Ser Asp Asn Glu Asn Arg Met Glu Glu Ser Lys Ala Leu Phe Arg
                245                 250                 255
Thr Ile Ile Thr Tyr Pro Trp Phe Gln Asn Ser Ser Val Ile Leu Phe
            260                 265                 270
Leu Asn Lys Lys Asp Leu Leu Glu Glu Lys Ile Met Tyr Ser His Leu
        275                 280                 285
Val Asp Tyr Phe Pro Glu Tyr Asp Gly Pro Gln Arg Asp Ala Gln Ala
    290                 295                 300
```

```
Ala Arg Glu Phe Ile Leu Lys Met Phe Val Asp Leu Asn Pro Asp Ser
305                 310                 315                 320

Asp Lys Ile Ile Tyr Ser His Phe Thr Cys Ala Thr Asp Thr Glu Asn
            325                 330                 335

Ile Arg Phe Val Phe Ala Ala Val Lys Asp Thr Ile Leu Gln Leu Asn
        340                 345                 350

Leu Lys Glu Tyr Asn Leu Val
        355

<210> SEQ ID NO 10
<211> LENGTH: 359
<212> TYPE: PRT
<213> ORGANISM: Mus sp.

<400> SEQUENCE: 10

Met Thr Leu Glu Ser Ile Met Ala Cys Cys Leu Ser Glu Glu Ala Lys
1               5                   10                  15

Glu Ala Arg Arg Ile Asn Asp Glu Ile Glu Arg Gln Leu Arg Arg Asp
            20                  25                  30

Lys Arg Asp Ala Arg Arg Glu Leu Lys Leu Leu Leu Leu Gly Thr Gly
        35                  40                  45

Glu Ser Gly Lys Ser Thr Phe Ile Lys Gln Met Arg Ile Ile His Gly
    50                  55                  60

Ser Asp Tyr Ser Asp Glu Asp Lys Arg Gly Phe Thr Lys Leu Val Tyr
65                  70                  75                  80

Gln Asn Ile Phe Thr Ala Met Gln Ala Met Ile Arg Ala Met Asp Thr
                85                  90                  95

Leu Lys Ile Pro Tyr Lys Tyr Glu His Asn Lys Ala His Ala Gln Leu
            100                 105                 110

Val Arg Glu Val Asp Val Glu Lys Val Ser Ala Phe Asp Val Pro Asp
        115                 120                 125

Tyr Ala Ala Ile Lys Ser Leu Trp Asn Asp Pro Gly Ile Gln Glu Cys
130                 135                 140

Tyr Asp Arg Arg Arg Glu Tyr Gln Leu Ser Asp Ser Thr Lys Tyr Tyr
145                 150                 155                 160

Leu Asn Asp Leu Asp Arg Val Ala Asp Pro Ser Tyr Leu Pro Thr Gln
                165                 170                 175

Gln Asp Val Leu Arg Val Arg Val Pro Thr Thr Gly Ile Ile Glu Tyr
            180                 185                 190

Pro Phe Asp Leu Gln Ser Val Ile Phe Arg Met Val Asp Val Gly Gly
        195                 200                 205

Gln Arg Ser Glu Arg Arg Lys Trp Ile His Cys Phe Glu Asn Val Thr
    210                 215                 220

Ser Ile Met Phe Leu Val Ala Leu Ser Glu Tyr Asp Gln Val Leu Val
225                 230                 235                 240

Glu Ser Asp Asn Glu Asn Arg Met Glu Glu Ser Lys Ala Leu Phe Arg
                245                 250                 255

Thr Ile Ile Thr Tyr Pro Trp Phe Gln Asn Ser Ser Val Ile Leu Phe
            260                 265                 270

Leu Asn Lys Lys Asp Leu Leu Glu Glu Lys Ile Met Tyr Ser His Leu
        275                 280                 285

Val Asp Tyr Phe Pro Glu Tyr Asp Gly Pro Gln Arg Asp Ala Gln Ala
    290                 295                 300

Ala Arg Glu Phe Ile Leu Lys Met Phe Val Asp Leu Asn Pro Asp Ser
305                 310                 315                 320
```

```
Asp Lys Ile Ile Tyr Ser His Phe Thr Cys Ala Thr Asp Thr Glu Asn
            325                 330                 335

Ile Arg Phe Val Phe Ala Ala Val Lys Asp Thr Ile Leu Gln Leu Asn
            340                 345                 350

Leu Lys Glu Tyr Asn Leu Val
        355
```

<210> SEQ ID NO 11
<211> LENGTH: 359
<212> TYPE: PRT
<213> ORGANISM: Mus sp.

<400> SEQUENCE: 11

```
Met Thr Leu Glu Ser Ile Met Ala Cys Cys Leu Ser Glu Glu Ala Lys
 1               5                  10                  15

Glu Ala Arg Arg Ile Asn Asp Glu Ile Glu Arg His Val Arg Arg Asp
            20                  25                  30

Lys Arg Asp Ala Arg Arg Glu Leu Lys Leu Leu Leu Leu Gly Thr Gly
        35                  40                  45

Glu Ser Gly Lys Ser Thr Phe Ile Lys Gln Met Arg Ile Ile His Gly
    50                  55                  60

Ser Asp Tyr Ser Asp Glu Asp Lys Arg Gly Phe Thr Lys Leu Val Tyr
65                  70                  75                  80

Gln Asn Ile Phe Thr Ala Met Gln Ala Met Ile Arg Ala Met Asp Thr
                85                  90                  95

Leu Lys Ile Pro Tyr Lys Tyr Glu His Asn Lys Ala His Ala Gln Leu
            100                 105                 110

Val Arg Glu Val Asp Val Glu Lys Val Ser Ala Phe Asp Val Pro Asp
        115                 120                 125

Tyr Ala Ala Ile Lys Ser Leu Trp Asn Asp Pro Gly Ile Gln Glu Cys
130                 135                 140

Tyr Asp Arg Arg Arg Glu Tyr Gln Leu Ser Asp Ser Thr Lys Tyr Tyr
145                 150                 155                 160

Leu Asn Asp Leu Asp Arg Val Ala Asp Pro Ser Tyr Leu Pro Thr Gln
                165                 170                 175

Gln Asp Val Leu Arg Val Arg Val Pro Thr Thr Gly Ile Ile Glu Tyr
            180                 185                 190

Pro Phe Asp Leu Gln Ser Val Ile Phe Arg Met Val Asp Val Gly Gly
        195                 200                 205

Gln Arg Ser Glu Arg Arg Lys Trp Ile His Cys Phe Glu Asn Val Thr
    210                 215                 220

Ser Ile Met Phe Leu Val Ala Leu Ser Glu Tyr Asp Gln Val Leu Val
225                 230                 235                 240

Glu Ser Asp Asn Glu Asn Arg Met Glu Glu Ser Lys Ala Leu Phe Arg
                245                 250                 255

Thr Ile Ile Thr Tyr Pro Trp Phe Gln Asn Ser Ser Val Ile Leu Phe
            260                 265                 270

Leu Asn Lys Lys Asp Leu Leu Glu Glu Lys Ile Met Tyr Ser His Leu
        275                 280                 285

Val Asp Tyr Phe Pro Glu Tyr Asp Gly Pro Gln Arg Asp Ala Gln Ala
    290                 295                 300

Ala Arg Glu Phe Ile Leu Lys Met Phe Val Asp Leu Asn Pro Asp Ser
305                 310                 315                 320

Asp Lys Ile Ile Tyr Ser His Phe Thr Cys Ala Thr Asp Thr Glu Asn
```

```
                    325                 330                 335
Ile Arg Phe Val Phe Ala Ala Val Lys Asp Thr Ile Leu Gln Leu Asn
            340                 345                 350

Leu Lys Glu Tyr Asn Leu Val
        355

<210> SEQ ID NO 12
<211> LENGTH: 359
<212> TYPE: PRT
<213> ORGANISM: Mus sp.

<400> SEQUENCE: 12

Met Thr Leu Glu Ser Ile Met Ala Cys Cys Leu Ser Glu Glu Ala Lys
  1               5                  10                  15

Glu Ala Arg Arg Ile Asn Asp Glu Ile Glu Arg His Val Arg Arg Asp
                 20                  25                  30

Lys Arg Asp Ala Arg Arg Glu Leu Lys Leu Leu Leu Leu Gly Thr Gly
             35                  40                  45

Glu Ser Gly Lys Ser Thr Phe Ile Lys Gln Met Arg Ile Ile His Gly
 50                  55                  60

Ser Gly Tyr Ser Asp Glu Asp Lys Arg Gly Phe Thr Lys Leu Val Tyr
 65                  70                  75                  80

Gln Asn Ile Phe Thr Ala Met Gln Ala Met Ile Arg Ala Met Asp Thr
                 85                  90                  95

Leu Lys Ile Pro Tyr Lys Tyr Glu His Asn Lys Ala His Ala Gln Leu
            100                 105                 110

Val Arg Glu Val Asp Val Glu Lys Val Ser Ala Phe Asp Val Pro Asp
        115                 120                 125

Tyr Ala Ala Ile Lys Ser Leu Trp Asn Asp Pro Gly Ile Gln Glu Cys
130                 135                 140

Tyr Asp Arg Arg Arg Glu Tyr Gln Leu Ser Asp Ser Thr Lys Tyr Tyr
145                 150                 155                 160

Leu Asn Asp Leu Asp Arg Val Ala Asp Pro Ser Tyr Leu Pro Thr Gln
                165                 170                 175

Gln Asp Val Leu Arg Val Arg Val Pro Thr Thr Gly Ile Ile Glu Tyr
            180                 185                 190

Pro Phe Asp Leu Gln Ser Val Ile Phe Arg Met Val Asp Val Gly Gly
        195                 200                 205

Gln Arg Ser Glu Arg Arg Lys Trp Ile His Cys Phe Glu Asn Val Thr
210                 215                 220

Ser Ile Met Phe Leu Val Ala Leu Ser Glu Tyr Asp Gln Val Leu Val
225                 230                 235                 240

Glu Ser Asp Asn Glu Asn Arg Met Glu Glu Ser Lys Ala Leu Phe Arg
                245                 250                 255

Thr Ile Ile Thr Tyr Pro Trp Phe Gln Asn Ser Ser Val Ile Leu Phe
            260                 265                 270

Leu Asn Lys Lys Asp Leu Leu Glu Glu Lys Ile Met Tyr Ser His Leu
        275                 280                 285

Val Asp Tyr Phe Pro Glu Tyr Asp Gly Pro Gln Arg Asp Ala Gln Ala
    290                 295                 300

Ala Arg Glu Phe Ile Leu Lys Met Phe Val Asp Leu Asn Pro Asp Ser
305                 310                 315                 320

Asp Lys Ile Ile Tyr Ser His Phe Thr Cys Ala Thr Asp Thr Glu Asn
                325                 330                 335
```

```
Ile Arg Phe Val Phe Ala Ala Val Lys Asp Thr Ile Leu Gln Leu Asn
            340                 345                 350

Leu Lys Asp Cys Gly Leu Phe
        355
```

<210> SEQ ID NO 13
<211> LENGTH: 359
<212> TYPE: PRT
<213> ORGANISM: Mus sp.

<400> SEQUENCE: 13

```
Met Thr Leu Glu Ser Ile Met Ala Cys Cys Leu Ser Glu Glu Ala Lys
  1               5                  10                  15

Glu Ala Arg Arg Ile Asn Asp Glu Ile Glu Arg His Val Arg Arg Asp
             20                  25                  30

Lys Arg Asp Ala Arg Arg Glu Leu Lys Leu Leu Leu Leu Gly Thr Gly
         35                  40                  45

Glu Ser Gly Lys Ser Thr Phe Ile Lys Gln Met Arg Ile Ile His Gly
 50                  55                  60

Ser Asp Tyr Ser Asp Glu Asp Lys Arg Gly Phe Thr Lys Leu Val Tyr
 65                  70                  75                  80

Gln Asn Ile Phe Thr Ala Met Gln Ala Met Ile Arg Ala Met Asp Thr
                 85                  90                  95

Leu Lys Ile Pro Tyr Lys Tyr Glu His Asn Lys Ala His Ala Gln Leu
            100                 105                 110

Val Arg Glu Val Asp Val Glu Lys Val Ser Ala Phe Asp Val Pro Asp
        115                 120                 125

Tyr Ala Ala Ile Lys Ser Leu Trp Asn Asp Pro Gly Ile Gln Glu Cys
130                 135                 140

Tyr Asp Arg Arg Arg Glu Tyr Gln Leu Ser Asp Ser Thr Lys Tyr Tyr
145                 150                 155                 160

Leu Asn Asp Leu Asp Arg Val Ala Asp Pro Ser Tyr Leu Pro Thr Gln
                165                 170                 175

Gln Asp Val Leu Arg Val Arg Val Pro Thr Thr Gly Ile Ile Glu Tyr
            180                 185                 190

Pro Phe Asp Leu Gln Ser Val Ile Phe Arg Met Val Asp Val Gly Gly
        195                 200                 205

Gln Arg Ser Glu Arg Arg Lys Trp Ile His Cys Phe Glu Asn Val Thr
210                 215                 220

Ser Ile Met Phe Leu Val Ala Leu Ser Glu Tyr Asp Gln Val Leu Val
225                 230                 235                 240

Glu Ser Asp Asn Glu Asn Arg Met Glu Glu Ser Lys Ala Leu Phe Arg
                245                 250                 255

Thr Ile Ile Thr Tyr Pro Trp Phe Gln Asn Ser Ser Val Ile Leu Phe
            260                 265                 270

Leu Asn Lys Lys Asp Leu Leu Glu Glu Lys Ile Met Tyr Ser His Leu
        275                 280                 285

Val Asp Tyr Phe Pro Glu Tyr Asp Gly Pro Gln Arg Asp Ala Gln Ala
290                 295                 300

Ala Arg Glu Phe Ile Leu Lys Met Phe Val Asp Leu Asn Pro Asp Ser
305                 310                 315                 320

Asp Lys Ile Ile Tyr Ser His Phe Thr Cys Ala Thr Asp Thr Glu Asn
                325                 330                 335

Ile Arg Phe Val Phe Ala Ala Val Lys Asp Thr Ile Leu Gln Leu Asn
            340                 345                 350
```

```
Leu Lys Asp Cys Gly Leu Phe
        355

<210> SEQ ID NO 14
<211> LENGTH: 353
<212> TYPE: PRT
<213> ORGANISM: Mus sp.

<400> SEQUENCE: 14

Met Ala Cys Cys Leu Ser Glu Glu Ala Lys Glu Ala Arg Arg Ile Asn
  1               5                  10                  15

Asp Glu Ile Glu Arg His Val Arg Arg Asp Lys Arg Asp Ala Arg Arg
             20                  25                  30

Glu Leu Lys Leu Leu Leu Gly Thr Gly Glu Ser Gly Lys Ser Thr
         35                  40                  45

Phe Ile Lys Gln Met Arg Ile Ile His Gly Ser Asp Tyr Ser Asp Glu
     50                  55                  60

Asp Lys Arg Gly Phe Thr Lys Leu Val Tyr Gln Asn Ile Phe Thr Ala
 65                  70                  75                  80

Met Gln Ala Met Ile Arg Ala Met Asp Thr Leu Lys Ile Pro Tyr Lys
                 85                  90                  95

Tyr Glu His Asn Lys Ala His Ala Gln Leu Val Arg Glu Val Asp Val
                100                 105                 110

Glu Lys Val Ser Ala Phe Asp Val Pro Asp Tyr Ala Ala Ile Lys Ser
            115                 120                 125

Leu Trp Asn Asp Pro Gly Ile Gln Glu Cys Tyr Asp Arg Arg Arg Glu
    130                 135                 140

Tyr Gln Leu Ser Asp Ser Thr Lys Tyr Tyr Leu Asn Asp Leu Asp Arg
145                 150                 155                 160

Val Ala Asp Pro Ser Tyr Leu Pro Thr Gln Gln Asp Val Leu Arg Val
                165                 170                 175

Arg Val Pro Thr Thr Gly Ile Ile Glu Tyr Pro Phe Asp Leu Gln Ser
            180                 185                 190

Val Ile Phe Arg Met Val Asp Val Gly Gly Gln Arg Ser Glu Arg Arg
        195                 200                 205

Lys Trp Ile His Cys Phe Glu Asn Val Thr Ser Ile Met Phe Leu Val
    210                 215                 220

Ala Leu Ser Glu Tyr Asp Gln Val Leu Val Glu Ser Asp Asn Glu Asn
225                 230                 235                 240

Arg Met Glu Glu Ser Lys Ala Leu Phe Arg Thr Ile Ile Thr Tyr Pro
                245                 250                 255

Trp Phe Gln Asn Ser Ser Val Ile Leu Phe Leu Asn Lys Lys Asp Leu
            260                 265                 270

Leu Glu Glu Lys Ile Met Tyr Ser His Leu Val Asp Tyr Phe Pro Glu
        275                 280                 285

Tyr Asp Gly Pro Gln Arg Asp Ala Gln Ala Arg Glu Phe Ile Leu
    290                 295                 300

Lys Met Phe Val Asp Leu Asn Pro Asp Ser Asp Lys Ile Ile Tyr Ser
305                 310                 315                 320

His Phe Thr Cys Ala Thr Asp Thr Glu Asn Ile Arg Phe Val Phe Ala
                325                 330                 335

Ala Val Lys Asp Thr Ile Leu Gln Leu Asn Leu Lys Gln Tyr Glu Leu
            340                 345                 350

Leu
```

<210> SEQ ID NO 15
<211> LENGTH: 359
<212> TYPE: PRT
<213> ORGANISM: Homo sapiens

<400> SEQUENCE: 15

Met Thr Leu Glu Ser Ile Met Ala Cys Cys Leu Ser Glu Ala Lys
1               5                   10                  15

Glu Ala Arg Arg Ile Asn Asp Glu Ile Glu Arg Gln Leu Arg Arg Asp
            20                  25                  30

Lys Arg Asp Ala Arg Arg Glu Leu Lys Leu Leu Leu Gly Thr Gly
            35                  40                  45

Glu Ser Gly Lys Ser Thr Phe Ile Lys Gln Met Arg Ile Ile His Gly
    50                  55                  60

Ser Gly Tyr Ser Asp Glu Asp Lys Arg Gly Phe Thr Lys Leu Val Tyr
65              70                  75                  80

Gln Asn Ile Phe Thr Ala Met Gln Ala Met Ile Arg Ala Met Asp Thr
                85                  90                  95

Leu Lys Ile Pro Tyr Lys Tyr Glu His Asn Lys Ala His Ala Gln Leu
            100                 105                 110

Val Arg Glu Val Asp Val Glu Lys Val Ser Ala Phe Glu Asn Pro Tyr
        115                 120                 125

Val Asp Ala Ile Lys Ser Leu Trp Asn Asp Pro Gly Ile Gln Glu Cys
130                 135                 140

Tyr Asp Arg Arg Arg Glu Tyr Gln Leu Ser Asp Ser Thr Lys Tyr Tyr
145                 150                 155                 160

Leu Asn Asp Leu Asp Arg Val Ala Asp Pro Ala Tyr Leu Pro Thr Gln
                165                 170                 175

Gln Asp Val Leu Arg Val Arg Val Pro Thr Thr Gly Ile Ile Glu Tyr
            180                 185                 190

Pro Phe Asp Leu Gln Ser Val Ile Phe Arg Met Val Asp Val Gly Gly
        195                 200                 205

Gln Arg Ser Glu Arg Arg Lys Trp Ile His Cys Phe Glu Asn Val Thr
210                 215                 220

Ser Ile Met Phe Leu Val Ala Leu Ser Glu Tyr Asp Gln Val Leu Val
225                 230                 235                 240

Glu Ser Asp Asn Glu Asn Arg Met Glu Glu Ser Lys Ala Leu Phe Arg
                245                 250                 255

Thr Ile Ile Thr Tyr Pro Trp Phe Gln Asn Ser Ser Val Ile Leu Phe
            260                 265                 270

Leu Asn Lys Lys Asp Leu Leu Glu Glu Lys Ile Met Tyr Ser His Leu
        275                 280                 285

Val Asp Tyr Phe Pro Glu Tyr Asp Gly Pro Gln Arg Asp Ala Gln Ala
290                 295                 300

Ala Arg Glu Phe Ile Leu Lys Met Phe Val Asp Leu Asn Pro Asp Ser
305                 310                 315                 320

Asp Lys Ile Asn Tyr Ser His Phe Thr Cys Ala Thr Asp Thr Glu Asn
                325                 330                 335

Ile Arg Phe Val Phe Ala Ala Val Lys Asp Thr Ile Leu Gln Leu Asn
            340                 345                 350

Leu Lys Glu Tyr Asn Ala Val
        355

-continued

<210> SEQ ID NO 16
<211> LENGTH: 353
<212> TYPE: PRT
<213> ORGANISM: Homo sapiens

<400> SEQUENCE: 16

Met Ala Cys Cys Leu Ser Glu Glu Ala Lys Glu Ala Arg Arg Ile Asn
 1               5                  10                  15

Asp Glu Ile Glu Arg Gln Leu Arg Arg Asp Lys Arg Asp Ala Arg Arg
            20                  25                  30

Glu Leu Lys Leu Leu Leu Leu Gly Thr Gly Glu Ser Gly Lys Ser Thr
        35                  40                  45

Phe Ile Lys Gln Met Arg Ile Ile His Gly Ser Gly Tyr Ser Asp Glu
    50                  55                  60

Asp Lys Arg Gly Phe Thr Lys Leu Val Tyr Gln Asn Ile Phe Thr Ala
65                  70                  75                  80

Met Gln Ala Met Ile Arg Ala Met Asp Thr Leu Lys Ile Pro Tyr Lys
                85                  90                  95

Tyr Glu His Asn Lys Ala His Ala Gln Leu Val Arg Glu Val Asp Val
            100                 105                 110

Glu Lys Val Ser Ala Phe Glu Asn Pro Tyr Val Asp Ala Ile Lys Ser
        115                 120                 125

Leu Trp Asn Asp Pro Gly Ile Gln Glu Cys Tyr Asp Arg Arg Arg Glu
    130                 135                 140

Tyr Gln Leu Ser Asp Ser Thr Lys Tyr Tyr Leu Asn Asp Leu Asp Arg
145                 150                 155                 160

Val Ala Asp Pro Ala Tyr Leu Pro Thr Gln Gln Asp Val Leu Arg Val
                165                 170                 175

Arg Val Pro Thr Thr Gly Ile Ile Glu Tyr Pro Phe Asp Leu Gln Ser
            180                 185                 190

Val Ile Phe Arg Met Val Asp Val Gly Gly Gln Arg Ser Glu Arg Arg
        195                 200                 205

Lys Trp Ile His Cys Phe Glu Asn Val Thr Ser Ile Met Phe Leu Val
    210                 215                 220

Ala Leu Ser Glu Tyr Asp Gln Val Leu Val Glu Ser Asp Asn Glu Asn
225                 230                 235                 240

Arg Met Glu Glu Ser Lys Ala Leu Phe Arg Thr Ile Ile Thr Tyr Pro
                245                 250                 255

Trp Phe Gln Asn Ser Ser Val Ile Leu Phe Leu Asn Lys Lys Asp Leu
            260                 265                 270

Leu Glu Glu Lys Ile Met Tyr Ser His Leu Val Asp Tyr Phe Pro Glu
        275                 280                 285

Tyr Asp Gly Pro Gln Arg Asp Ala Gln Ala Ala Arg Glu Phe Ile Leu
    290                 295                 300

Lys Met Phe Val Asp Leu Asn Pro Asp Ser Asp Lys Ile Ile Tyr Ser
305                 310                 315                 320

His Phe Thr Cys Ala Thr Asp Thr Glu Asn Ile Arg Phe Val Phe Ala
                325                 330                 335

Ala Val Lys Asp Thr Ile Leu Gln Leu Asn Leu Lys Glu Tyr Asn Ala
            340                 345                 350

Val

<210> SEQ ID NO 17
<211> LENGTH: 353
<212> TYPE: PRT

<213> ORGANISM: Homo sapiens

<400> SEQUENCE: 17

```
Met Ala Cys Cys Leu Ser Glu Ala Lys Glu Ala Arg Arg Ile Asn
 1               5                  10                  15
Asp Glu Ile Glu Arg His Val Arg Arg Asp Lys Arg Asp Ala Arg Arg
             20                  25                  30
Glu Leu Lys Leu Leu Leu Gly Thr Gly Glu Ser Gly Lys Ser Thr
         35                  40                  45
Phe Ile Lys Gln Met Arg Ile Ile His Gly Ser Asp Tyr Ser Asp Glu
 50                  55                  60
Asp Lys Arg Gly Phe Thr Lys Leu Val Tyr Gln Asn Ile Phe Thr Ala
 65                  70                  75                  80
Met Gln Ala Met Ile Arg Ala Met Asp Thr Leu Lys Ile Pro Tyr Lys
                 85                  90                  95
Tyr Glu His Asn Lys Ala His Ala Gln Leu Val Arg Glu Val Asp Val
                100                 105                 110
Glu Lys Val Ser Ala Phe Asp Val Pro Asp Tyr Ala Ala Ile Lys Ser
            115                 120                 125
Leu Trp Asn Asp Pro Gly Ile Gln Glu Cys Tyr Asp Arg Arg Arg Glu
130                 135                 140
Tyr Gln Leu Ser Asp Ser Thr Lys Tyr Tyr Leu Asn Asp Leu Asp Arg
145                 150                 155                 160
Val Ala Asp Pro Ala Tyr Leu Pro Thr Gln Gln Asp Val Leu Arg Val
                165                 170                 175
Arg Val Pro Thr Thr Gly Ile Ile Glu Tyr Pro Phe Asp Leu Gln Ser
            180                 185                 190
Val Ile Phe Arg Met Val Asp Val Gly Gly Gln Arg Ser Glu Arg Arg
        195                 200                 205
Lys Trp Ile His Cys Phe Glu Asn Val Thr Ser Ile Met Phe Leu Val
210                 215                 220
Ala Leu Ser Glu Tyr Asp Gln Val Leu Val Glu Ser Asp Asn Glu Asn
225                 230                 235                 240
Arg Met Glu Glu Ser Lys Ala Leu Phe Arg Thr Ile Ile Thr Tyr Pro
                245                 250                 255
Trp Phe Gln Asn Ser Ser Val Ile Leu Phe Leu Asn Lys Lys Asp Leu
            260                 265                 270
Leu Glu Glu Lys Ile Met Tyr Ser His Leu Val Asp Tyr Phe Pro Glu
        275                 280                 285
Tyr Asp Gly Pro Gln Arg Asp Ala Gln Ala Ala Arg Glu Phe Ile Leu
290                 295                 300
Lys Met Phe Val Asp Leu Asn Pro Asp Ser Asp Lys Ile Ile Tyr Ser
305                 310                 315                 320
His Phe Thr Cys Ala Thr Asp Thr Glu Asn Ile Arg Phe Val Phe Ala
                325                 330                 335
Ala Val Lys Asp Thr Ile Leu Gln Leu Asn Leu Lys Glu Tyr Asn Leu
            340                 345                 350
Val
```

<210> SEQ ID NO 18
<211> LENGTH: 354
<212> TYPE: PRT
<213> ORGANISM: Homo sapiens

<400> SEQUENCE: 18

```
Met Ala Cys Cys Leu Ser Glu Glu Ala Lys Glu Ala Arg Arg Ile Asn
 1               5                  10                  15

Asp Glu Ile Glu Arg His Val Arg Arg Asp Lys Arg Asp Ala Arg Arg
             20                  25                  30

Glu Leu Lys Leu Leu Leu Gly Thr Gly Glu Ser Gly Lys Ser Thr
         35                  40                  45

Phe Ile Lys Gln Met Arg Ile Ile His Gly Ser Asp Tyr Ser Asp Glu
     50                  55                  60

Asp Lys Arg Gly Phe Thr Lys Leu Val Tyr Gln Asn Ile Phe Thr Ala
 65                  70                  75                  80

Met Gln Ala Met Ile Arg Ala Met Asp Thr Leu Lys Ile Pro Tyr Lys
                 85                  90                  95

Tyr Glu His Asn Lys Ala His Ala Gln Leu Val Arg Glu Val Asp Val
                100                 105                 110

Glu Lys Val Ser Ala Phe Asp Val Pro Asp Tyr Ala Ala Ile Lys Ser
             115                 120                 125

Leu Trp Asn Asp Pro Gly Ile Gln Glu Cys Tyr Asp Arg Arg Arg Glu
130                 135                 140

Tyr Gln Leu Ser Asp Ser Thr Lys Tyr Tyr Leu Asn Asp Leu Asp Arg
145                 150                 155                 160

Val Ala Asp Pro Ala Tyr Leu Pro Thr Gln Gln Asp Val Leu Arg Val
                165                 170                 175

Arg Val Pro Thr Thr Gly Ile Ile Glu Tyr Pro Phe Asp Leu Gln Ser
                180                 185                 190

Val Ile Phe Arg Met Val Asp Val Gly Gly Gln Arg Ser Glu Arg Arg
         195                 200                 205

Lys Trp Ile His Cys Phe Glu Asn Val Thr Ser Ile Met Phe Leu Val
         210                 215                 220

Ala Leu Ser Glu Tyr Asp Gln Val Leu Val Glu Ser Asp Asn Glu Asn
225                 230                 235                 240

Arg Met Glu Glu Ser Lys Ala Leu Phe Arg Thr Ile Ile Thr Tyr Pro
                245                 250                 255

Trp Phe Gln Asn Ser Ser Val Ile Leu Phe Leu Asn Lys Lys Asp Leu
                260                 265                 270

Leu Glu Glu Lys Ile Met Tyr Ser His Leu Val Asp Tyr Phe Pro Glu
            275                 280                 285

Tyr Asp Gly Pro Gln Arg Asp Ala Gln Ala Ala Arg Glu Phe Ile Leu
            290                 295                 300

Lys Met Phe Val Asp Leu Asn Pro Asp Ser Asp Lys Ile Ile Tyr Ser
305                 310                 315                 320

His Phe Thr Cys Ala Thr Asp Thr Gln Asn Val Lys Phe Val Asp Ala
                325                 330                 335

Val Thr Asp Ile Ile Ile Lys Glu Asn Leu Asn Leu Lys Asp Cys Gly
                340                 345                 350

Leu  Phe

<210> SEQ ID NO 19
<211> LENGTH: 354
<212> TYPE: PRT
<213> ORGANISM: Homo sapiens

<400> SEQUENCE: 19

Met Ala Cys Cys Leu Ser Glu Glu Ala Lys Glu Ala Arg Arg Ile Asn
 1               5                  10                  15
```

```
Asp Glu Ile Glu Arg His Val Arg Arg Asp Lys Arg Asp Ala Arg Arg
             20                  25                  30

Glu Leu Lys Leu Leu Leu Gly Thr Gly Glu Ser Gly Lys Ser Thr
         35                  40                  45

Phe Ile Lys Gln Met Arg Ile Ile His Gly Ser Asp Tyr Ser Asp Glu
         50                  55                  60

Asp Lys Arg Gly Phe Thr Lys Leu Val Tyr Gln Asn Ile Phe Thr Ala
 65                  70                  75                  80

Met Gln Ala Met Ile Arg Ala Met Asp Thr Leu Lys Ile Pro Tyr Lys
                 85                  90                  95

Tyr Glu His Asn Lys Ala His Ala Gln Leu Val Arg Glu Val Asp Val
             100                 105                 110

Glu Lys Val Ser Ala Phe Asp Val Pro Asp Tyr Ala Ala Ile Lys Ser
         115                 120                 125

Leu Trp Asn Asp Pro Gly Ile Gln Glu Cys Tyr Asp Arg Arg Arg Glu
     130                 135                 140

Tyr Gln Leu Ser Asp Ser Thr Lys Tyr Tyr Leu Asn Asp Leu Asp Arg
145                 150                 155                 160

Val Ala Asp Pro Ala Tyr Leu Pro Thr Gln Gln Asp Val Leu Arg Val
                 165                 170                 175

Arg Val Pro Thr Thr Gly Ile Ile Glu Tyr Pro Phe Asp Leu Gln Ser
             180                 185                 190

Val Ile Phe Arg Met Val Asp Val Gly Gly Gln Arg Ser Glu Arg Arg
         195                 200                 205

Lys Trp Ile His Cys Phe Glu Asn Val Thr Ser Ile Met Phe Leu Val
     210                 215                 220

Ala Leu Ser Glu Tyr Asp Gln Val Leu Val Glu Ser Asp Asn Glu Asn
225                 230                 235                 240

Arg Met Glu Glu Ser Lys Ala Leu Phe Arg Thr Ile Ile Thr Tyr Pro
                 245                 250                 255

Trp Phe Gln Asn Ser Ser Val Ile Leu Phe Leu Asn Lys Lys Asp Leu
             260                 265                 270

Leu Glu Glu Lys Ile Met Tyr Ser His Leu Val Asp Tyr Phe Pro Glu
         275                 280                 285

Tyr Asp Gly Pro Gln Arg Asp Ala Gln Ala Ala Arg Glu Phe Ile Leu
     290                 295                 300

Lys Met Phe Val Asp Asn Met Arg Arg Asp Val Lys Glu Ile Ile Tyr
305                 310                 315                 320

Ser His Phe Thr Cys Ala Thr Asp Thr Glu Asn Ile Arg Phe Val Phe
                 325                 330                 335

Ala Ala Val Lys Asp Thr Ile Leu Gln Leu Asn Leu Lys Asp Cys Gly
             340                 345                 350

Leu Phe

<210> SEQ ID NO 20
<211> LENGTH: 359
<212> TYPE: PRT
<213> ORGANISM: Homo sapiens

<400> SEQUENCE: 20

Met Thr Leu Glu Ser Ile Met Ala Cys Cys Leu Ser Glu Glu Ala Lys
 1               5                  10                  15

Glu Ala Arg Arg Ile Asn Asp Glu Ile Glu Arg Gln Leu Arg Arg Asp
             20                  25                  30
```

```
Lys Arg Asp Ala Arg Arg Glu Leu Lys Leu Leu Leu Gly Thr Gly
         35                  40                  45

Glu Ser Gly Lys Ser Thr Phe Ile Lys Gln Met Arg Ile Ile His Gly
         50                  55                  60

Ser Asp Tyr Ser Asp Glu Asp Lys Arg Gly Phe Thr Lys Leu Val Tyr
 65                  70                  75                  80

Gln Asn Ile Phe Thr Ala Met Gln Ala Met Ile Arg Ala Met Asp Thr
                 85                  90                  95

Leu Lys Ile Pro Tyr Lys Tyr Glu His Asn Lys Ala His Ala Gln Leu
            100                 105                 110

Val Arg Glu Val Asp Val Glu Lys Val Ser Ala Phe Asp Val Pro Asp
        115                 120                 125

Tyr Ala Ala Ile Lys Ser Leu Trp Asn Asp Pro Gly Ile Gln Glu Cys
    130                 135                 140

Tyr Asp Arg Arg Arg Glu Tyr Gln Leu Ser Asp Ser Thr Lys Tyr Tyr
145                 150                 155                 160

Leu Asn Asp Leu Asp Arg Val Ala Asp Pro Ala Tyr Leu Pro Thr Gln
                165                 170                 175

Gln Asp Val Leu Arg Val Arg Val Pro Thr Thr Gly Ile Ile Glu Tyr
            180                 185                 190

Pro Phe Asp Leu Gln Ser Val Ile Phe Arg Met Val Asp Val Gly Gly
        195                 200                 205

Gln Arg Ser Glu Arg Arg Lys Trp Ile His Cys Phe Glu Asn Val Thr
    210                 215                 220

Ser Ile Met Phe Leu Val Ala Leu Ser Glu Tyr Asp Gln Val Leu Val
225                 230                 235                 240

Glu Ser Asp Asn Glu Asn Arg Met Glu Glu Ser Lys Ala Leu Phe Arg
                245                 250                 255

Thr Ile Ile Thr Tyr Pro Trp Phe Gln Asn Ser Ser Val Ile Leu Phe
            260                 265                 270

Leu Asn Lys Lys Asp Leu Leu Glu Glu Lys Ile Met Tyr Ser His Leu
        275                 280                 285

Val Asp Tyr Phe Pro Glu Tyr Asp Gly Pro Gln Arg Asp Ala Gln Ala
    290                 295                 300

Ala Arg Glu Phe Ile Leu Lys Met Phe Val Asp Leu Asn Pro Asp Ser
305                 310                 315                 320

Asp Lys Ile Ile Tyr Ser His Phe Thr Cys Ala Thr Asp Thr Glu Asn
                325                 330                 335

Ile Arg Phe Val Phe Ala Ala Val Lys Asp Thr Ile Leu Gln Leu Asn
            340                 345                 350

Leu Lys Glu Tyr Asn Leu Val
        355

<210> SEQ ID NO 21
<211> LENGTH: 359
<212> TYPE: PRT
<213> ORGANISM: Homo sapiens

<400> SEQUENCE: 21

Met Thr Leu Glu Ser Ile Met Ala Cys Cys Leu Ser Glu Glu Ala Lys
 1               5                  10                  15

Glu Ala Arg Arg Ile Asn Asp Glu Ile Glu Arg His Val Arg Arg Asp
                20                  25                  30

Lys Arg Asp Ala Arg Arg Glu Leu Lys Leu Leu Leu Leu Gly Thr Gly
```

```
            35                  40                  45
Glu Ser Gly Lys Ser Thr Phe Ile Lys Gln Met Arg Ile Ile His Gly
 50                  55                  60

Ser Asp Tyr Ser Asp Glu Asp Lys Arg Gly Phe Thr Lys Leu Val Tyr
 65                  70                  75                  80

Gln Asn Ile Phe Thr Ala Met Gln Ala Met Ile Arg Ala Met Asp Thr
                 85                  90                  95

Leu Lys Ile Pro Tyr Lys Tyr Glu His Asn Lys Ala His Ala Gln Leu
                100                 105                 110

Val Arg Glu Val Asp Val Glu Lys Val Ser Ala Phe Asp Val Pro Asp
            115                 120                 125

Tyr Ala Ala Ile Lys Ser Leu Trp Asn Asp Pro Gly Ile Gln Glu Cys
130                 135                 140

Tyr Asp Arg Arg Glu Tyr Gln Leu Ser Asp Ser Thr Lys Tyr Tyr
145                 150                 155                 160

Leu Asn Asp Leu Asp Arg Val Ala Asp Pro Ala Tyr Leu Pro Thr Gln
                165                 170                 175

Gln Asp Val Leu Arg Val Arg Val Pro Thr Thr Gly Ile Ile Glu Tyr
                180                 185                 190

Pro Phe Asp Leu Gln Ser Val Ile Phe Arg Met Val Asp Val Gly Gly
            195                 200                 205

Gln Arg Ser Glu Arg Arg Lys Trp Ile His Cys Phe Glu Asn Val Thr
210                 215                 220

Ser Ile Met Phe Leu Val Ala Leu Ser Glu Tyr Asp Gln Val Leu Val
225                 230                 235                 240

Glu Ser Asp Asn Glu Asn Arg Met Glu Glu Ser Lys Ala Leu Phe Arg
                245                 250                 255

Thr Ile Ile Thr Tyr Pro Trp Phe Gln Asn Ser Ser Val Ile Leu Phe
                260                 265                 270

Leu Asn Lys Lys Asp Leu Leu Glu Glu Lys Ile Met Tyr Ser His Leu
            275                 280                 285

Val Asp Tyr Phe Pro Glu Tyr Asp Gly Pro Gln Arg Asp Ala Gln Ala
290                 295                 300

Ala Arg Glu Phe Ile Leu Lys Met Phe Val Asp Leu Asn Pro Asp Ser
305                 310                 315                 320

Asp Lys Ile Ile Tyr Ser His Phe Thr Cys Ala Thr Asp Thr Glu Asn
                325                 330                 335

Ile Arg Phe Val Phe Ala Ala Val Lys Asp Thr Ile Leu Gln Leu Asn
                340                 345                 350

Leu Lys Glu Tyr Asn Leu Val
        355

<210> SEQ ID NO 22
<211> LENGTH: 359
<212> TYPE: PRT
<213> ORGANISM: Homo sapiens

<400> SEQUENCE: 22

Met Thr Leu Glu Ser Ile Met Ala Cys Cys Leu Ser Glu Glu Ala Lys
 1               5                  10                  15

Glu Ala Arg Arg Ile Asn Asp Glu Ile Glu Arg His Val Arg Arg Asp
                20                  25                  30

Lys Arg Asp Ala Arg Arg Glu Leu Lys Leu Leu Leu Leu Gly Thr Gly
            35                  40                  45
```

```
Glu Ser Gly Lys Ser Thr Phe Ile Lys Gln Met Arg Ile Ile His Gly
 50                  55                  60

Ser Gly Tyr Ser Asp Glu Asp Lys Arg Gly Phe Thr Lys Leu Val Tyr
 65                  70                  75                   80

Gln Asn Ile Phe Thr Ala Met Gln Ala Met Ile Arg Ala Met Asp Thr
                 85                  90                  95

Leu Lys Ile Pro Tyr Lys Tyr Glu His Asn Lys Ala His Ala Gln Leu
                100                 105                 110

Val Arg Glu Val Asp Val Glu Lys Val Ser Ala Phe Asp Val Pro Asp
            115                 120                 125

Tyr Ala Ala Ile Lys Ser Leu Trp Asn Asp Pro Gly Ile Gln Glu Cys
130                 135                 140

Tyr Asp Arg Arg Glu Tyr Gln Leu Ser Asp Ser Thr Lys Tyr Tyr
145                 150                 155                 160

Leu Asn Asp Leu Asp Arg Val Ala Asp Pro Ala Tyr Leu Pro Thr Gln
                165                 170                 175

Gln Asp Val Leu Arg Val Arg Val Pro Thr Thr Gly Ile Ile Glu Tyr
            180                 185                 190

Pro Phe Asp Leu Gln Ser Val Ile Phe Arg Met Val Asp Val Gly Gly
        195                 200                 205

Gln Arg Ser Glu Arg Arg Lys Trp Ile His Cys Phe Glu Asn Val Thr
210                 215                 220

Ser Ile Met Phe Leu Val Ala Leu Ser Glu Tyr Asp Gln Val Leu Val
225                 230                 235                 240

Glu Ser Asp Asn Glu Asn Arg Met Glu Glu Ser Lys Ala Leu Phe Arg
                245                 250                 255

Thr Ile Ile Thr Tyr Pro Trp Phe Gln Asn Ser Ser Val Ile Leu Phe
                260                 265                 270

Leu Asn Lys Lys Asp Leu Leu Glu Glu Lys Ile Met Tyr Ser His Leu
            275                 280                 285

Val Asp Tyr Phe Pro Glu Tyr Asp Gly Pro Gln Arg Asp Ala Gln Ala
        290                 295                 300

Ala Arg Glu Phe Ile Leu Lys Met Phe Val Asp Leu Asn Pro Asp Ser
305                 310                 315                 320

Asp Lys Ile Ile Tyr Ser His Phe Thr Cys Ala Thr Asp Thr Glu Asn
                325                 330                 335

Ile Arg Phe Val Phe Ala Ala Val Lys Asp Thr Ile Leu Gln Leu Asn
                340                 345                 350

Leu Lys Asp Cys Gly Leu Phe
355

<210> SEQ ID NO 23
<211> LENGTH: 359
<212> TYPE: PRT
<213> ORGANISM: Homo sapiens

<400> SEQUENCE: 23

Met Thr Leu Glu Ser Ile Met Ala Cys Cys Leu Ser Glu Glu Ala Lys
  1               5                  10                  15

Glu Ala Arg Arg Ile Asn Asp Glu Ile Glu Arg His Val Arg Arg Asp
                 20                  25                  30

Lys Arg Asp Ala Arg Arg Glu Leu Lys Leu Leu Leu Leu Gly Thr Gly
             35                  40                  45

Glu Ser Gly Lys Ser Thr Phe Ile Lys Gln Met Arg Ile Ile His Gly
 50                  55                  60
```

```
Ser Asp Tyr Ser Asp Glu Asp Lys Arg Gly Phe Thr Lys Leu Val Tyr
 65                  70                  75                  80

Gln Asn Ile Phe Thr Ala Met Gln Ala Met Ile Arg Ala Met Asp Thr
                 85                  90                  95

Leu Lys Ile Pro Tyr Lys Tyr Glu His Asn Lys Ala His Ala Gln Leu
            100                 105                 110

Val Arg Glu Val Asp Val Glu Lys Val Ser Ala Phe Asp Val Pro Asp
        115                 120                 125

Tyr Ala Ala Ile Lys Ser Leu Trp Asn Asp Pro Gly Ile Gln Glu Cys
130                 135                 140

Tyr Asp Arg Arg Glu Tyr Gln Leu Ser Asp Ser Thr Lys Tyr Tyr
145                 150                 155                 160

Leu Asn Asp Leu Asp Arg Val Ala Asp Pro Ala Tyr Leu Pro Thr Gln
                165                 170                 175

Gln Asp Val Leu Arg Val Arg Val Pro Thr Thr Gly Ile Ile Glu Tyr
            180                 185                 190

Pro Phe Asp Leu Gln Ser Val Ile Phe Arg Met Val Asp Val Gly Gly
        195                 200                 205

Gln Arg Ser Glu Arg Arg Lys Trp Ile His Cys Phe Glu Asn Val Thr
210                 215                 220

Ser Ile Met Phe Leu Val Ala Leu Ser Glu Tyr Asp Gln Val Leu Val
225                 230                 235                 240

Glu Ser Asp Asn Glu Asn Arg Met Glu Glu Ser Lys Ala Leu Phe Arg
                245                 250                 255

Thr Ile Ile Thr Tyr Pro Trp Phe Gln Asn Ser Ser Val Ile Leu Phe
            260                 265                 270

Leu Asn Lys Lys Asp Leu Leu Glu Glu Lys Ile Met Tyr Ser His Leu
        275                 280                 285

Val Asp Tyr Phe Pro Glu Tyr Asp Gly Pro Gln Arg Asp Ala Gln Ala
290                 295                 300

Ala Arg Glu Phe Ile Leu Lys Met Phe Val Asp Leu Asn Pro Asp Ser
305                 310                 315                 320

Asp Lys Ile Asn Tyr Ser His Phe Thr Cys Ala Thr Asp Thr Glu Asn
                325                 330                 335

Ile Arg Phe Val Phe Ala Ala Val Lys Asp Thr Ile Leu Gln Leu Asn
            340                 345                 350

Leu Lys Asp Cys Gly Leu Phe
        355

<210> SEQ ID NO 24
<211> LENGTH: 353
<212> TYPE: PRT
<213> ORGANISM: Homo sapiens

<400> SEQUENCE: 24

Met Ala Cys Cys Leu Ser Glu Glu Ala Lys Glu Ala Arg Arg Ile Asn
 1               5                  10                  15

Asp Glu Ile Glu Arg His Val Arg Arg Asp Lys Arg Asp Ala Arg Arg
                20                  25                  30

Glu Leu Lys Leu Leu Leu Leu Gly Thr Gly Glu Ser Gly Lys Ser Thr
            35                  40                  45

Phe Ile Lys Gln Met Arg Ile Ile His Gly Ser Asp Tyr Ser Asp Glu
        50                  55                  60

Asp Lys Arg Gly Phe Thr Lys Leu Val Tyr Gln Asn Ile Phe Thr Ala
```

```
            65                  70                  75                  80
Met Gln Ala Met Ile Arg Ala Met Asp Thr Leu Lys Ile Pro Tyr Lys
                85                  90                  95

Tyr Glu His Asn Lys Ala His Ala Gln Leu Val Arg Glu Val Asp Val
            100                 105                 110

Glu Lys Val Ser Ala Phe Asp Val Pro Asp Tyr Ala Ala Ile Lys Ser
        115                 120                 125

Leu Trp Asn Asp Pro Gly Ile Gln Glu Cys Tyr Asp Arg Arg Arg Glu
    130                 135                 140

Tyr Gln Leu Ser Asp Ser Thr Lys Tyr Leu Asn Asp Leu Asp Arg
145                 150                 155                 160

Val Ala Asp Pro Ala Tyr Leu Pro Thr Gln Gln Asp Val Leu Arg Val
                165                 170                 175

Arg Val Pro Thr Thr Gly Ile Ile Glu Tyr Pro Phe Asp Leu Gln Ser
            180                 185                 190

Val Ile Phe Arg Met Val Asp Val Gly Gly Gln Arg Ser Glu Arg Arg
        195                 200                 205

Lys Trp Ile His Cys Phe Glu Asn Val Thr Ser Ile Met Phe Leu Val
    210                 215                 220

Ala Leu Ser Glu Tyr Asp Gln Val Leu Val Glu Ser Asp Asn Glu Asn
225                 230                 235                 240

Arg Met Glu Glu Ser Lys Ala Leu Phe Arg Thr Ile Ile Thr Tyr Pro
                245                 250                 255

Trp Phe Gln Asn Ser Ser Val Ile Leu Phe Leu Asn Lys Lys Asp Leu
            260                 265                 270

Leu Glu Glu Lys Ile Met Tyr Ser His Leu Val Asp Tyr Phe Pro Glu
        275                 280                 285

Tyr Asp Gly Pro Gln Arg Asp Ala Gln Ala Ala Arg Glu Phe Ile Leu
    290                 295                 300

Lys Met Phe Val Asp Leu Asn Pro Asp Ser Asp Lys Ile Ile Tyr Ser
305                 310                 315                 320

His Phe Thr Cys Ala Thr Asp Thr Glu Asn Ile Arg Phe Val Phe Ala
                325                 330                 335

Ala Val Lys Asp Thr Ile Leu Gln Leu Asn Leu Lys Gln Tyr Glu Leu
            340                 345                 350

Leu

<210> SEQ ID NO 25
<211> LENGTH: 359
<212> TYPE: PRT
<213> ORGANISM: Homo sapiens

<400> SEQUENCE: 25

Met Thr Leu Glu Ser Ile Met Ala Cys Cys Leu Ser Glu Glu Ala Lys
1               5                   10                  15

Glu Ala Arg Arg Ile Asn Asp Glu Ile Glu Arg His Val Arg Arg Asp
            20                  25                  30

Lys Arg Asp Ala Arg Arg Glu Leu Lys Leu Leu Leu Leu Gly Thr Gly
        35                  40                  45

Glu Ser Gly Lys Ser Thr Phe Ile Lys Gln Met Arg Ile Ile His Gly
    50                  55                  60

Ser Gly Tyr Ser Asp Glu Asp Lys Arg Gly Phe Thr Lys Leu Val Tyr
65                  70                  75                  80

Gln Asn Ile Phe Thr Ala Met Gln Ala Met Ile Arg Ala Met Asp Thr
```

```
                85                  90                  95
Leu Lys Ile Pro Tyr Lys Tyr Glu His Asn Lys Ala His Ala Gln Leu
            100                 105                 110
Val Arg Glu Val Asp Val Glu Lys Val Ser Ala Phe Asp Val Pro Asp
        115                 120                 125
Tyr Ala Ile Lys Ser Leu Trp Asn Asp Pro Gly Ile Gln Glu Cys
    130                 135                 140
Tyr Asp Arg Arg Glu Tyr Gln Leu Ser Asp Ser Thr Lys Tyr Tyr
145                 150                 155                 160
Leu Asn Asp Leu Asp Arg Val Ala Asp Pro Ala Tyr Leu Pro Thr Gln
                165                 170                 175
Gln Asp Val Leu Arg Val Arg Val Pro Thr Thr Gly Ile Ile Glu Tyr
            180                 185                 190
Pro Phe Asp Leu Gln Ser Val Ile Phe Arg Met Val Asp Val Gly Gly
        195                 200                 205
Gln Arg Ser Glu Arg Arg Lys Trp Ile His Cys Phe Glu Asn Val Thr
    210                 215                 220
Ser Ile Met Phe Leu Val Ala Leu Ser Glu Tyr Asp Gln Val Leu Val
225                 230                 235                 240
Glu Ser Asp Asn Glu Asn Arg Met Glu Glu Ser Lys Ala Leu Phe Arg
                245                 250                 255
Thr Ile Ile Thr Tyr Pro Trp Phe Gln Asn Ser Ser Val Ile Leu Phe
            260                 265                 270
Leu Asn Lys Lys Asp Leu Leu Glu Glu Lys Ile Met Tyr Ser His Leu
        275                 280                 285
Val Asp Tyr Phe Pro Glu Tyr Asp Gly Pro Gln Arg Asp Ala Gln Ala
    290                 295                 300
Ala Arg Glu Phe Ile Leu Lys Met Phe Val Asp Leu Asn Pro Asp Ser
305                 310                 315                 320
Asp Lys Ile Ile Tyr Ser His Phe Thr Cys Ala Thr Asp Thr Glu Asn
                325                 330                 335
Ile Arg Phe Val Phe Ala Ala Val Lys Asp Thr Ile Leu Gln Leu Asn
            340                 345                 350
Leu Lys Gln Tyr Glu Leu Leu
        355

<210> SEQ ID NO 26
<211> LENGTH: 359
<212> TYPE: PRT
<213> ORGANISM: Homo sapiens

<400> SEQUENCE: 26

Met Thr Leu Glu Ser Ile Met Ala Cys Cys Leu Ser Glu Glu Ala Lys
  1               5                  10                  15
Glu Ala Arg Arg Ile Asn Asp Glu Ile Glu Arg His Val Arg Arg Asp
                20                  25                  30
Lys Arg Asp Ala Arg Arg Glu Leu Lys Leu Leu Leu Leu Gly Thr Gly
        35                  40                  45
Glu Ser Gly Lys Ser Thr Phe Ile Lys Gln Met Arg Ile Ile His Gly
    50                  55                  60
Ser Asp Tyr Ser Asp Glu Asp Lys Arg Gly Phe Thr Lys Leu Val Tyr
65                  70                  75                  80
Gln Asn Ile Phe Thr Ala Met Gln Ala Met Ile Arg Ala Met Asp Thr
                85                  90                  95
```

Leu Lys Ile Pro Tyr Lys Tyr Glu His Asn Lys Ala His Ala Gln Leu
                100                 105                 110

Val Arg Glu Val Asp Val Glu Lys Val Ser Ala Phe Asp Val Pro Asp
            115                 120                 125

Tyr Ala Ala Ile Lys Ser Leu Trp Asn Asp Pro Gly Ile Gln Glu Cys
130                 135                 140

Tyr Asp Arg Arg Glu Tyr Gln Leu Ser Asp Ser Thr Lys Tyr Tyr
145                 150                 155                 160

Leu Asn Asp Leu Asp Arg Val Ala Asp Pro Ala Tyr Leu Pro Thr Gln
                165                 170                 175

Gln Asp Val Leu Arg Val Arg Val Pro Thr Thr Gly Ile Ile Glu Tyr
            180                 185                 190

Pro Phe Asp Leu Gln Ser Val Ile Phe Arg Met Val Asp Val Gly Gly
195                 200                 205

Gln Arg Ser Glu Arg Arg Lys Trp Ile His Cys Phe Glu Asn Val Thr
            210                 215                 220

Ser Ile Met Phe Leu Val Ala Leu Ser Glu Tyr Asp Gln Val Leu Val
225                 230                 235                 240

Glu Ser Asp Asn Glu Asn Arg Met Glu Glu Ser Lys Ala Leu Phe Arg
                245                 250                 255

Thr Ile Ile Thr Tyr Pro Trp Phe Gln Asn Ser Ser Val Ile Leu Phe
            260                 265                 270

Leu Asn Lys Lys Asp Leu Leu Glu Glu Lys Ile Met Tyr Ser His Leu
            275                 280                 285

Val Asp Tyr Phe Pro Glu Tyr Asp Gly Pro Gln Arg Asp Ala Gln Ala
290                 295                 300

Ala Arg Glu Phe Ile Leu Lys Met Phe Val Asp Leu Asn Pro Asp Ser
305                 310                 315                 320

Asp Lys Ile Ile Tyr Ser His Phe Thr Cys Ala Thr Asp Thr Glu Asn
                325                 330                 335

Ile Arg Phe Val Phe Ala Ala Val Lys Asp Thr Ile Leu Gln Leu Asn
            340                 345                 350

Leu Lys Gln Tyr Glu Leu Leu
        355

<210> SEQ ID NO 27
<211> LENGTH: 983
<212> TYPE: DNA
<213> ORGANISM: Artificial Sequence
<220> FEATURE:
<223> OTHER INFORMATION: Description of Artificial Sequence: Synthetic
    nucleotide sequence

<400> SEQUENCE: 27
atggcccggt ccctgacttg gggctgctgt ccctggtgcc tgacagagga ggagaagact    60
gccgccagaa tcgaccagga gatcaacagg attttgttgg aacagaaaaa acaagagcgc   120
gaggaattga aactcctgct gttggggcct ggtgagagcg gaagagtac gttcatcaag    180 cagatgcgca tcattcacgg tgtgggctac tcggaggagg accgcagagc cttccggctg   240
ctcatctacc agaacatctt cgtctccatg caggccatga tagatgcgat ggaccggctg   300
cagatcccct tcagcaggcc tgacagcaag cagcacgcca gcctagtgat gacccaggac   360
ccctataaag tgagcacatt cgagaagcca tatgcagtgg ccatgcagta cctgtggcgg   420
gacgcgggca tccgtgcatg ctacgagcga aggcgtgaat tccaccttct ggactccgcg   480
gtgtattacc tgtcacacct gggcgtagga aatggattca ctgttttgag aacgtgattg   540

```
ccctcatcta cctggcctcc ctgagcgagt atgaccagtg cctagaggag aacgatcagg    600
agaaccgcat ggaggagagt ctcgctctgt tcagcacgat cctagagctg ccctggttca    660
agagcacctc ggtcatcctc ttcctcaaca agacggacat cctggaagat aagattcaca    720
cctcccacct ggccacatac ttccccagct tccagggacc ccggcgagac gcagaggccg    780
ccaagagctt catcttggac atgtatgcgc gcgtgtacgc gagctgcgca gagccccagg    840
acggtggcag gaaaggctcc cgcgcgcgcc gcttcttcgc acacttcacc tgtgccacgg    900
acacgcaaag cgtccgcagc gtgttcaagg acgtgcggga ctcggtgctg gcccggtacc    960
tggacgagat caacctgctg tga                                            983
```

```
<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gactgtggcc tcttctga                                                   18

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gagtacaatc tggtctga                                                   18

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
cagtatgagc tcttgtga                                                   18

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gagtgcggcc tctactga                                                   18

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
```

```
ggatgcggac tctactga                                                     18
```

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33

```
tacatcggcc tctgctga                                                     18
```

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34

```
gacatcatgc tccaatga                                                     18
```

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35

```
caactaatgc tccaatga                                                     18
```

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36

```
caccaggttg aactctga                                                     18
```

<210> SEQ ID NO 37
<211> LENGTH: 359
<212> TYPE: PRT
<213> ORGANISM: Homo sapiens

<400> SEQUENCE: 37

```
Met Thr Leu Glu Ser Ile Met Ala Cys Cys Leu Ser Glu Glu Ala Lys
 1               5                  10                  15

Glu Ala Arg Arg Ile Asn Asp Glu Ile Glu Arg Gln Leu Arg Arg Asp
            20                  25                  30

Lys Arg Asp Ala Arg Arg Glu Leu Lys Leu Leu Leu Leu Gly Thr Gly
        35                  40                  45

Glu Ser Gly Lys Ser Thr Phe Ile Lys Gln Met Arg Ile Ile His Gly
    50                  55                  60

Ser Gly Tyr Ser Asp Glu Asp Lys Arg Gly Phe Thr Lys Leu Val Tyr
65                  70                  75                  80

Gln Asn Ile Phe Thr Ala Met Gln Ala Met Ile Arg Ala Met Asp Thr
```

```
                       85                  90                  95
Leu Lys Ile Pro Tyr Lys Tyr Glu His Asn Lys Ala His Ala Gln Leu
                100                 105                 110
Val Arg Glu Val Asp Val Glu Lys Val Ser Ala Phe Glu Asn Pro Tyr
            115                 120                 125
Val Asp Ala Ile Lys Ser Leu Trp Asn Asp Pro Gly Ile Gln Glu Cys
        130                 135                 140
Tyr Asp Arg Arg Glu Tyr Gln Leu Ser Asp Ser Thr Lys Tyr Tyr
145                 150                 155                 160
Leu Asn Asp Leu Asp Arg Val Ala Asp Pro Ala Tyr Leu Pro Thr Gln
                165                 170                 175
Gln Asp Val Leu Arg Val Arg Val Pro Thr Thr Gly Ile Ile Glu Tyr
            180                 185                 190
Pro Phe Asp Leu Gln Ser Val Ile Phe Arg Met Val Asp Val Gly Gly
        195                 200                 205
Gln Arg Ser Glu Arg Arg Lys Trp Ile His Cys Phe Glu Asn Val Thr
    210                 215                 220
Ser Ile Met Phe Leu Val Ala Leu Ser Glu Tyr Asp Gln Val Leu Val
225                 230                 235                 240
Glu Ser Asp Asn Glu Asn Arg Met Glu Glu Ser Lys Ala Leu Phe Arg
                245                 250                 255
Thr Ile Ile Thr Tyr Pro Trp Phe Gln Asn Ser Ser Val Ile Leu Phe
            260                 265                 270
Leu Asn Lys Lys Asp Leu Leu Glu Glu Lys Ile Met Tyr Ser His Leu
        275                 280                 285
Val Asp Tyr Phe Pro Glu Tyr Asp Gly Pro Gln Arg Asp Ala Gln Ala
    290                 295                 300
Ala Arg Glu Phe Ile Leu Lys Met Phe Val Asp Leu Asn Pro Asp Ser
305                 310                 315                 320
Asp Lys Ile Asn Tyr Ser His Phe Thr Cys Ala Thr Asp Thr Glu Asn
                325                 330                 335
Ile Arg Phe Val Phe Ala Ala Val Lys Asp Thr Ile Leu Gln Leu Asn
            340                 345                 350
Leu Lys Glu Tyr Asn Leu Val
        355

<210> SEQ ID NO 38
<211> LENGTH: 374
<212> TYPE: PRT
<213> ORGANISM: Homo sapiens

<400> SEQUENCE: 38

Met Ala Arg Ser Leu Thr Trp Gly Cys Cys Pro Trp Cys Leu Thr Glu
1               5                   10                  15
Glu Glu Lys Thr Ala Ala Arg Ile Asp Gln Glu Ile Asn Arg Ile Leu
                20                  25                  30
Leu Glu Gln Lys Lys Gln Glu Arg Glu Glu Leu Lys Leu Leu Leu Leu
            35                  40                  45
Gly Pro Gly Glu Ser Gly Lys Ser Thr Phe Ile Lys Gln Met Arg Ile
        50                  55                  60
Ile His Gly Val Gly Tyr Ser Glu Glu Asp Arg Arg Ala Phe Arg Leu
65                  70                  75                  80
Leu Ile Tyr Gln Asn Ile Phe Val Ser Met Gln Ala Met Ile Asp Ala
                85                  90                  95
```

-continued

```
Met Asp Arg Leu Gln Ile Pro Phe Ser Arg Pro Asp Ser Lys Gln His
            100                 105                 110

Ala Ser Leu Val Met Thr Gln Asp Pro Tyr Lys Val Ser Thr Phe Glu
        115                 120                 125

Lys Pro Tyr Ala Val Ala Met Gln Tyr Leu Trp Arg Asp Ala Gly Ile
130                 135                 140

Arg Ala Cys Tyr Glu Arg Arg Glu Phe His Leu Leu Asp Ser Ala
145                 150                 155                 160

Val Tyr Tyr Leu Ser His Leu Glu Arg Ile Ser Glu Asp Ser Tyr Ile
                165                 170                 175

Pro Thr Ala Gln Asp Val Leu Arg Ser Arg Met Pro Thr Thr Gly Ile
            180                 185                 190

Asn Glu Tyr Cys Phe Ser Val Lys Lys Thr Lys Leu Arg Ile Val Asp
        195                 200                 205

Val Gly Gly Gln Arg Ser Glu Arg Arg Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asp Gln Glu Asn Arg Met Glu Glu Ser Leu Ala
                245                 250                 255

Leu Phe Ser Thr Ile Leu Glu Leu Pro Trp Phe Lys Ser Thr Ser Val
            260                 265                 270

Ile Leu Phe Leu Asn Lys Thr Asp Ile Leu Glu Asp Lys Ile His Thr
        275                 280                 285

Ser His Leu Ala Thr Tyr Phe Pro Ser Phe Gln Gly Pro Arg Arg Asp
290                 295                 300

Ala Glu Ala Ala Lys Ser Phe Ile Leu Asp Met Tyr Ala Arg Val Tyr
305                 310                 315                 320

Ala Ser Cys Ala Glu Pro Gln Asp Gly Gly Arg Lys Gly Ser Arg Ala
                325                 330                 335

Arg Arg Phe Phe Ala His Phe Thr Cys Ala Thr Asp Thr Gln Ser Val
            340                 345                 350

Arg Ser Val Phe Lys Asp Val Arg Asp Ser Val Leu Ala Arg Tyr Leu
        355                 360                 365

Asp Glu Ile Asn Leu Leu
    370
```

<210> SEQ ID NO 39
<211> LENGTH: 374
<212> TYPE: PRT
<213> ORGANISM: Homo sapiens

<400> SEQUENCE: 39

```
Met Ala Arg Ser Leu Thr Trp Arg Cys Cys Pro Trp Cys Leu Thr Glu
1               5                   10                  15

Asp Glu Lys Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu
        35                  40                  45

Gly Pro Gly Glu Ser Gly Lys Ser Thr Phe Ile Lys Gln Met Arg Ile
50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95
```

-continued

```
Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
    130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175
Pro Thr Ala Gln Asp Val Leu Arg Ser Arg Met Pro Thr Thr Gly Ile
            180                 185                 190
Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
    210                 215                 220

Asn Val Ile Ala Leu Ile Tyr Leu Ala Ser Leu Ser Glu Tyr Asp Gln
225                 230                 235                 240
Cys Leu Glu Glu Asn Asn Gln Glu Asn Arg Met Lys Glu Ser Leu Ala
                245                 250                 255
Leu Phe Gly Thr Ile Leu Glu Leu Pro Trp Phe Lys Ser Thr Ser Val
            260                 265                 270
Ile Leu Phe Leu Asn Lys Thr Asp Ile Leu Glu Glu Lys Ile Pro Thr
        275                 280                 285
Ser His Leu Ala Thr Tyr Phe Pro Ser Phe Gln Gly Pro Lys Gln Asp
    290                 295                 300
Ala Glu Ala Ala Lys Arg Phe Ile Leu Asp Met Tyr Thr Arg Met Tyr
305                 310                 315                 320
Thr Gly Cys Val Asp Gly Pro Glu Gly Ser Lys Lys Gly Ala Arg Ser
                325                 330                 335
Arg Arg Leu Phe Ser His Tyr Thr Cys Ala Thr Asp Thr Gln Asn Ile
            340                 345                 350
Arg Lys Val Phe Lys Asp Val Arg Asp Ser Val Leu Ala Arg Tyr Leu
        355                 360                 365
Asp Glu Ile Asn Leu Leu
    370
```

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Illustrative N-terminal peptide sequence

<400> SEQUENCE: 40

```
Met Thr Leu Glu Ser Ile
  1               5
```

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: Synthetic hemaglutinin epitope tag

<400> SEQUENCE: 41

```
Asp Val Pro Asp Tyr Ala
  1               5

<210> SEQ ID NO 42
<211> LENGTH: 11
<212> TYPE: DNA
<213> ORGANISM: Artificial Sequence
<220> FEATURE:
<223> OTHER INFORMATION: Description of Artificial Sequence:
      Illustrative oligonucleotide

<400> SEQUENCE: 42
ggcgcgccgc c                                                                11
```